United States Patent [19]
Johnson et al.

[11] Patent Number: 5,019,508
[45] Date of Patent: May 28, 1991

[54] SYNOVIAL PHOSPHOLIPASES

[75] Inventors: Lorin K. Johnson, Pleasanton; Jeffrey J. Seilhamer, Milpitas, both of Calif.; Waldemar Pruzanski; Peter Vadas, both of Ontario, Canada

[73] Assignees: Biotechnology Research Partners, Ltd., Calif.; The University of Toronto Innovations Foundation, Ontario, Canada

[21] Appl. No.: 215,726

[22] Filed: Jul. 6, 1988

Related U.S. Application Data

[63] Continuation-in-part of Ser. No. 89,883, Aug. 27, 1987, abandoned.

[51] Int. Cl.$^5$ .................... C12N 9/20; C12N 15/55; C07H 15/12
[52] U.S. Cl. .................... 435/198; 435/172.1; 435/320.1; 435/252.3; 536/27; 935/14
[58] Field of Search .................... 435/172.3, 198, 320, 435/240.2, 252.3, 235, 255; 935/14, 28, 29, 31, 56, 58, 69, 71, 72; 536/27

[56] References Cited
PUBLICATIONS

Tanaka et al. *Gene* 64:257–264 (1988).
Geus et al. *Nucleic Acids Research* 15(9):3743–3759 (1987).
O'Hara et al., (1976) *J. Biochem.* 99:733–739.
Dufton et al., (1983) *Eur. J. Biochem.* 137:537–544.
Grataroli et al., (1982) *Eur. J. Biochem.* 122:111–117.
Reneseder et al., (1985) *J. Bio. Chem.* 260:11627–11634.
Pruzanski et al., (1986) *J. Invest. Dermatol.* 86:380–383.
Verger et al., (1982) *Biochem.* 21:6883–6889.
Gray et al., (1982) *Can. J. Biochim.* 60:108–117.
DeWinter et al., (1982) *Biochim. Biophys. Acta* 712:332–341.
Franson et al., (1982) *Lung* 160:275–284.
Garcia et al., (1975) *Biochim. Biophys. Res. Comm.* 64:128–135.
Sahu et al., (1977) *Biochim. Biophys. Acta* 489:307–317.
Verger et al., (1982) *Biochem.* 21:6883–6889.
Teramoto et al., (1983) *J. Biochim.* 93:1353–1360.
Trotter et al., (1986) *Neurochem. Res.* 11:349–361.
Lanni et al., (1981) *Biochim. Biophys. Acta* 658:54–63.
Vadas et al., (1980) *Life Sciences* 26:1721–1729.
Vadas (1981) *Nature* 293:583–585.
Wightman et al., (1981) *Biochim. J.* 200:441–444.
Franson et al., (1973) *Biochim. Biophys. Acta* 296:365–373.
Traynor et al., (1981) *Biochim. Biophys. Acta* 665:571–577.
Franson et al., (1977) *Biochim. J.* 167:839–841.
Kramer et al., (1978) *Biochim. Biophys. Acta* 507:381–394.
Chang et al., (1986) *J. Immunol.* 136:1283–1287.
Jesse et al., (1979) *Biochim. Biophys. Acta* 575:467–470.
Apitz-Castro et al., (1979) *Biochim. Biophys. Res. Comm.* 91(1): 63–71.
Van Den Bosch (1980) *Biochim. Biophys. Acta* 604:191–246.
Vadas et al., (1984) *Adv. Inflammation Res.* 7:51–59.
Vadas et al., (1981) *Nature* 293:583–585.
Silverman et al., *American Rheumatism Association: 51st Annual Scientific Meeting* (9–13 Jun. 1987, Washington, D. C.).
Hayakawa et al., (1988) *J. Biochem.* 103:263–266.
Dutilh et al., (1981) *J. Sci. Food Agricul.* 32:451–458.
Mazeaud et al., (1976) *J. Fish Res. Board Can.* 33:1297–1303.
Hara et al., (1988) *J. Biochem.* 104:326–328.
Matsuda et al., (1987) *Res. Commun. in Chem. Path.*
(List continued on next page.)

Primary Examiner—Richard A. Schwartz
Assistant Examiner—Richard Lebovitz
Attorney, Agent, or Firm—Irell & Manella

[57] ABSTRACT

Mammalian synovial phospholipase $A_2$ (sPLA$_2$) enzymes are provided, as well as DNA constructs encoding these enzymes, methods of producing the enzymes recombinantly, and antibodies thereto. Therapeutic methods employing anti-synovial phospholipase antibodies are also provided, in addition to diagnositc methods and other applications of sPLA$_2$.

25 Claims, 11 Drawing Sheets

PUBLICATIONS

*Pharmacol.* 58(2):281–284.
Tojo et al., (1988) *J. Biol. Chem.* 263(12):5724–5734.
Ono et al., (1988) *J. Biol. Chem* 263(12):5732–5738.
Franson et al., (1978) *J. Lipid Res.* 19:18–23.
Stefanski et al., (1986) J. Biochem. 100:1297–1303.
Vadas et al.–(1985) Life Sciences 36:579–1303.
Pruzanski et al., (1985) Journal of Rheumatology 12(2):211–216.
Forst et al., (1986) Biochemistry 25:8381–8385.
Hayakawa et al., (1987) J. Biochem. 101–1311–1314.
Chang et al., (1987) J. Biochem. 102:147–154.
Nakaguchi et al., (1986) Enzyme 35:2–12.
Loeb et al., (1986) Journal of Biological Chemistry 261(23): 10467–10470.
Kramer et al., (1986) Biochim. Biophys. Acta 878:394–403.
Castle et al., (1981) Biochim. Biophys. Acta 666:259–274.
Gattaz et al., (1987) Biol. Psychiatry 22:421–426.
Horigome et al., (1987) J. Biochem. 101:625–631.
Bomalaski et al., (1986) Arthritis and Rheumatism 29(3):312–318.
Takano et al., (1987) Scand. J. Gastroenterol. 22:577–584.
Fawzy et al., (1987) Inflammation 11(4):389–400.
Chang et al., (1986) J. Biochem. 100:1099–1101.
Selihamer et al., (1986) DNA 5(6):519–527.
Huruki et al., (1986) J. Biochem. 99:99–109.
Han et al., (1987) Biochemistry 26:1617–1625.

FIG. 1

COMPARISON OF PLA₂ AMINO ACID SEQUENCES

```
                        1              10            20            30            40
Exon 2:
p Intestine             DLLNFRKMIK-LKTGKAPVPNYAFYGCYCGLGGKGSPKDATD?         +5  >9.6
rab Ascites             HLLDFRKMIR-YTTGKEAT?SYGAYGCSCGVGGR?APK?A            +5   10
r platelet,peri,spleen  ?LLEFGQMIL-FKTGKRADVSYGFYGCHCGVGGRGSPKDATDE h RASF-A    GLLQAHG     NLVNFHRMIK-LTTGKEAALSYGFYGCHCGVGGRGSPKDATDR        +2    5?
h RASF-B                ?LYLFKNMIQ-L
h cln 10    VPAVQG      GLLDLKSMIE-KVTGKNALTNYGFYGCYCGWGGRGTPKDGTDW        +1   ???
h NP        VVAAPTHS    SFWQFQRMVK-HITGRSAFFSYYGYGCYCGLGDKGIPVDDTDR        +3   ???
p NP        AVLAPTQS    AFWQFQRMVK-HITGWSALFSYYGYGCYCGLGGKGTPVDDTDR
r NP        GTTSTLS     SFWQFQRMVK-HITGRSAFFSYYGYGCYCGLGGRGIPVDATDR C. atrox                SLVQFETLIM-KIAGRSGLLWYSAYGCYCGWGGHGLPQDATDR        +1
A. pisc (K-49)          SVLELGKMIL-QETGKNAITSYGSYGCNCGWGHRGQPKDATDR        +2   >10

44         50           60           70          80      85
h Panc      VLLTVAAA DSGISPR AVWQFRKMIKCVIPGSDPFLEYNNYGCYCGLGGSGTPVDELDK    -1    6.0
p Panc      VGAA DSGISSR ALWQFRSMIKCAIPGSHPLMDFNNYGCYCGLGGSGTPVDELDK
r Panc      AGVT AHSISTR AVWQFRNMIKCTIPGSDPFREXNNYGCYCGLGGSGTPVDDLDR Exon 3:
p platelet   CCVTHECCYNRLEKS-GC-----GTKFLTYKFSYRGGQISCS
H RASF-A     CCVTHDCCYKRLEKR-GC-----GTKFLSYKFSNSGSRITC-
C. atrox     CCFVHDCCYG----KATDC-----NPKTVSYTYSEENGEIIC-
A. pisc      CCFVHKCCYK----KLTDC-----NHKTDRYSYSWKNKAIIC-
h panc       CCQTHDNCYDQAKILDSCKFLLDNPYTHTYSYSCSGSAITCS 86         90          100         110         120         130
Exon 4:
rab ascites        TNQDSCRKQLCQCDKAAAECFSRNKKSYSLKYQFYPNKFCK?YP-SC
rat platelet                                           QFYPANRCSGRPPSC
H RASF-A           AKQDSCRSQLCECDKAAATCFARNKTTYNKKYQYVSNKHCRGSTPRC
C. atrox           GGDDPCGTQICECDKAAAICFRDNIPSYDNKYWLFPPEDCREEPEPC
A. pisc            EEKNPCLKQMCECDKAVAICLRENLDTYNKKYAYFKLKCK-KPDTC
H panc             SKNKECEAFICNCDENAAICFSKAPYNKAHK-NLDTKKYCQS
```

FIG. 3

Screening oligos based upon RASF peak A Amino Acid Sequence:

```
1                                 16                   20                                  32        RASF-A
AsnLeuValAlaAsnPheHisArgMetIleLysLeuThrThrGlyLysGluAlaAlaLeuSerTyrGlyPheTyrGluPheTyrGlyCysHisCysGlyValGly    Clone 6
AATTTGGTGAATTTCCACAGAATGATCAAGTTGACGACAGAGAAAGGAAGCCGCACTCAGTTATGGCTTCTACGGCTGCCACTGTGGCGTGGGT
                                                                  Oligo 2779 -> 3'-TTTCTTCGGGGATAGGATGCTTAAGATGCCGACGGTTGACGCCGCATCC-5'
                                            3'-CATTTGAAGGTGTCTTACTAGTTTGATTGGTGGCCGTTTCTTCGGGGGA-5'  <- Oligo 2780
```

FIG. 5

```
5                                 24                                                            position #
PheHisArgMetIleLysLeuThrThrGlyLysGluAlaAlaLeuSerTyrGlyPheTyr                                     AA sequence
5'--TTCCACAGAATGATCAAGTTGACGACAGAGAAAGGAAGCCGCACTCAGTTATGGCTTCTAC-3'                              gene seq.
3'--AAGGTGTCTTACTAGTTCAACTGCTGTCTCTTCCTTCGGCGTGAGTCAATACCGAAGATG-5'                               Oligo 2905
```

FIG. 4-1

Human Genomic Clone 6 (Alu 404)
RASF Peak A Gene

```
      AluI Branch   DdeI                                              DdeI
      |---|         |-|                                               |-|
   1 AGCTGACCCCTGACCTCTGAGCATGGGGACAGCCCAGAAGGGAAGCACTCTTGTCCCCTTAGTTTTCT  69
     3      8      18                                              60
                      Sau3AI DdeI
                       |-|   |-|
  70 CTCCCATTGCAGTGATCCTCTCTCAGGGGGAAAAAGAAGCCATTGGGAGGAAGGAGAGTAGCAGAGA  138
                      83    92                             Acceptor StuI,HaeIII
                                                                   |----|
 139 GGGGCAGAGAGGGAGGGCACAGAGAACCCCATGCCCCATCACCAGACAACTCCCAAATTTCCTTCCAGGCC  207
                                                                  198  GlyL
         PstI,Sau96I,NcoI,HaeIII          Sau3AI,BclI     HincII              Fnu4HI
         |--||-||---|                      |----|         |-|                  |-|
 208 TACTGCAGGCCCATGGGAATTTGGTGAATTCCACAGAATGATCAAGTTGACGACAGGAAAGGAAGCCG  276
     euLeuGlnAlaHisGlyAsnLeuValAlaSnPheHisArgMetIleLysLeuThrThrGlyLysGluAlaA
                 217                        248                    257  275
      DdeI                       Fnu4HI BglI              BamHI,XhoI,Sau3AI
      |-|                         |-|   |-|                |----------|
 277 CACTCAGTTATGGCTTCTACGGGCTGCCACTGTGGGCGTGGGTGGCAGAGGATCCCCAAGGATGCAACGG  345
     laLeuSerTyrGlyPheTyrGlyCysHisCysGlyValGlyArgGlySerProLysAspAlaThrA
          280                       300    308             325           345
                                             HinfI   HhaI       AluI
      HaeIII                                  |-|    |-|         |-|
 346 ATCGGTGAGGCCACCTATCCCCTCCCCTACCCTCCTAGACTCTGCGCCAGGCAGGGCTGGGAGCT  408
     spArg 356                              382     390           407
```

FIG. 4-2

CLONE 10

```
                    DdeI      HinfI
  1 GGGGATGAAACTGAGGCTCTGACTTCCATTCAATACCATACTTTGAATTAGTGGCAGAGCCAGGATGAA  69
                      12        22                                                Intrn
                                               Intrn-branch
 70 CCCAGGTCTGCTCATTTCAATTCAAACTCTTAACCAGTTCTCCATACTGCTTGCACCTCCCTTCCCA 138
                                                                                  137
              Poly-A         AvaII, Sau96I
139 CTAAATGGAGAGAATAAAAAGAGACATGCAGGTCCCTCCAAGCCCTGGGTGGGAGAAAGGTAGGAGAT 207
                150                        170
       Sau96I,HaeIII                        Fnu4HI HphI              Acceptor
208 GTTGGGCAGTGGCCTAAAGCAGGGCTGGGCTGCCTGGGTGTCACCTGGGACATGGCTATCTTCCAG 276
               221                  239                                    270
                           AvaII,Sau96I      Sau3AI,TaqI,DpnI        HphI
277 GTGTGCCTGCTGTGCAAGGAGCTTGCTGGACCTAAAATCAATGATCAGAAGGTGACAGGAAGAACG 345
                                306                           322
    ValProAlaValGlnGlyLeuLeuAspLeuLysSerMETIleGluLysValThrGlyLysAsnA
                                                                              342
Intrn-branch                          Fnu4HI   Fnu4HI,HaeIII
346 CCCTGACAAACTACGGCTTCTACGGCTGTTACTGCGGCTGGGCCGAGGAACCCCAAGGATGGCA 414
                 427    434                      381                    390
    laLeuThrAsnTyrGlyPheTyrCysTyrCysGlyTrpGlyTyrGlyArgGlyThrProLysAspGlyT
    346
              AluI,Sau3AI,HphI   Acceptor,BglI
415 CCGATTGGTGAGCTGATCGCTATAACTGCCCTTTAGGCTCCAGGCTCTGCACCCATGTTTCTTATTCA 483
    hrAspTrp   427    434          444
484 ATTCCATATCAGTTCTGAAGATGAGTATTAAAGT 518
```

FIG. 6

```
      <1>
  1  GAATTCCCAACTCTGGAGTCCTCTGAGAGACCAAGGAGGAGCAGGGGAGGACGGC                      60
  1                                                                              60
 61  CGGGGCAGAAGTTGAGACCACCCAGCAGAGGAGCTAGGCCAGTCCATCTGCATTTGTCAC                 120
 61                                                                        <2>   120
121  CCAAGAACTCTTACCATGAAGACCCTCCTACTGTTGGCAGTGATCATGATCTTTGGCCTA                 180
121               MetLysThrLeuLeuLeuLeuAlaValIleMetIlePheGlyLeu                   180
121                -20                                                           180
181  CTGCAGGCCCATGGGAATTTGGTGAATTTCCACAGAATGATCAAGTTGACGACAGAAAG                  240
181  LeuGlnAlaHisGlyAsnLeuValAlaAsnPheHisArgMetIleLysLeuThrThrGlyLys              240
181                                +1                                            240
                                   T
241  GAAGCCCGCACTCAGTTATGGCTTCTACGGCTGCCACTGTGGCGTGGGTGGCAGAGGATCC                300
241  GluAlaAlaLeuSerTyrGlyPheTyrGlyCysHisCysGlyValGlyGlyArgGlySer                 300
241                   <3>                                                         300
301  CCCAAGGATGCAACGGATCGCTGCTGTGTCACTCATGACTGTTGCTACAAACGTCTGGAG                 360
301  ProLysAspAlaThrAspArgCysCysValThrHisAspCysCysTyrLysArgLeuGlu                 360
361  AAACGTGGATGTGCCACCAAATTCTGAGCTACAAGTTAGCAACTCGGGAGCAGAATC                    420
361  LysArgGlyCysGlyThrLysPheLeuSerTyrLysPheSerAsnSerGlySerArgIle                 420
361        <4>                                                                   420
421  ACCTGTGCAAAACAGGACTCCTGCAGAAGTCAACTGTGAGTGTGATAAGGCTGCTGCC                   480
421  ThrCysAlaLysGlnAspSerCysArgSerGlnLeuCysGluCysAspLysAlaAlaAla                 480
481  ACCTGTTTTGCTAGAAACAAGACGACTACAATAAAAGTACCAGTACTATTCCAATAA                    540
481  ThrCysPheAlaArgAsnLysThrThrTyrAsnLysLysTyrGlnTyrTyrSerAsnLys                 540
541  CACTGCAGAGGAGCACCCCTCGTGCTGAGTCCCCCCTCTTCCCTGAAACCTTCCACCCA                  600
541  HisCysArgGlySerThrProArgCys                                                  600
601  GTGCTGAATTCCCTCTCTCATACCCTCCCTCCCTACCCTAACCAAGTTCCTTGGCCATG                  660
661  CAGAAAGCATCCCTCACCCATCCTAGAGGCCAGGAGCCCTTCTATACCACCCAGA                      720
721  ATGAGACATCCAGCAGATTCCAGCCTTCTCCTCCACCTCAACCTCCGTGCTT                         780
781  AACCAAAGAAGCTGTACTCCGGGGTCTCTTCTGAATAAAGCAATTAGCAAATCAAAAA                   840
841  AAAAAAGGAATTC  854
841                 854

KEY:
     <1>  intron positions
     +1   amino acid positions
``` sPLA$_2$ Gene Sequence (Exons 1-5)

```
   1 GCAAGGGGCTCTAAGAATTGTAAGGGAACAGATGGATGTTCACAAGCACCACAGCCCTGGCCACATGACT 70
  71 TTTTAGGACTGGTATCGCAGAGTGTTTACTTAAGGCGGTGGAAGCTAAATTCTTAGCATGTGCTGGAGAG 140
 141 CATGAAAAGATATTTACTTTATGAATTAAAGCTGGAGTCAGTGTCAGCCCGAAGGTGAAGGAAAAAGAG 210
 211 CAACAGATCCAGGGAGCATTCACCTGCCCTGTCTCCAAACAGGTGAGGATGGGGAATAAAGTGAAGGGCA 280
 281 GTGCTTTGGTGGGAACTTCAAGGATACGCTCTGGCTTTTTCCAGGTTTAGAAGCTCATATGAGACAGGGG 350
 351 TGGAGGAAAAGAAGAAAGAAGAATAAGAAGAGAAAGTTGAGGCCCTGGCCCAAGTTAGTGGGAAGGAAAT 420
 421 CCACCCCATTAAACTCTCTCCCTGTGGACTTGGGTCACACGTGAGGCCTGCACAGTGCTGGAACATGGTA 490
 491 GAGGCCCAGGACATACTTCCTGTGAATGAATGATTGAGCGGCTGAATGAATGAGTACCGCTAAAAGCCCT 560
 561 CTTTTCTATTCCCAAATGCCACATTGAGCAGAAGGGAGCAGAGATCCTTGCTCAGCAATTGGTAGTCCCA 630
 631 TTTGGGTGTGCAAATGAGTCCACAGCCTGCAACAGCAGACAGTCTCTGCCCCCCTTAGAGGCGATTGCAG 700
 701 GGAGGTGGCTGACCGTTGATCACACCCAGAGGCTGGTTATGGGAATTTACTCCATGGAAAGACTCGGCAA 770
 771 AACTGCCTGAATGTGTTTTGGCATCAGGCTACTGACACGTAAGGGTTTCCCAATCCTCAACTCTGTCCTG 840
 841 GCCAGGCTGATGAGGGGAAGGAAAGGGATTACCTAGGGGTATGGGCGACCAATCCTGAGTCCACCAACTG 910
 911 ACCACGCCCATCCCCAGCCTTGTGCCTCACCTACCCCCAACCTCCAGAGGGAGCAGCTATTTAAGGGGAG 980
1>981 CAGGAGTGCAGAACAAACAAGACGGCCTGGGGATACAACTCTGGAGTCCTCTGAGAGGTAAAGAGCCAGC 1050
 1051 GAAGCTGATGTCCTGTCAAGAGCAGAATTC 1080
```

```
   1 GAATTCCTGCTCATTCGCTGCCTTTGAGAGTGGCTGTGTTGTGCATGCATGTGCATGATTTGATATGTAT 70
  71 GAGAGGGTGTGTGTGCATGAGTGTGTTGAGTGAGTATGTGAGTGTAGTGTAAGAGAGGATGTTGGCACTA 140
 141 TCAGGTAATTACGAGAGTGTGTGTATGTGGGCATAGGTGTGTTAACATGTATGTGTTTGGGAACTTGTGT 210
 211 ATGTGGAAGGGGTTAGAAGGCCTAGAAGAGAGAGGTTGATGCTTTCATTCTGGAGGAAAATACTGAGGCC 280
 281 GAGCCTCCATGGGTGCCTTGGAGACTCCAAGCCTTGAATCCAGTGTGGGGATATGCAAGCTATGTCTAGC 350
 351 GAGGGACACATCCTCTGACCTCAGGAACCTCCCAGGTAGTTGGGAGGAACCTGGTTCCAACCTCCCAAGA 420
 421 ACTCTCAGTCTGATGACGGTACAGGGGAGGTCTCATTAGTGTATCATGGGGTTCTCCACAGGTCTGAGGG 490
 491 CCTGATGTGTGTGAAACCATTCTGCAGAGCTGGGAACGGGTCAGGAGGTGGTTGTGTGTGTGTGTGTGTG 560
 561 TGTGTGTGCATTGCTGGAGGGCACTCCTTGTGTGCTCTGAGTGTGACAGAGGAAGTCACCCTGGACTTAG 630
2>631 GTTGGATGGGAGAGCCATGTCTGTGTGTCTCAGAGCCACCAAGGAGGAGCAGGGGAGCGACGGCCGGGGC 700
```

FIG. 7-1

```
2>  701 AGAAGTTGAGACCACCCAGCAGAGGAGCTAGGCCAGTCCATCTGCATTTGTCACCCAAGAACTCTTACCA 770
                                                                              M

2>  771 TGAAGACCCTCCTACTGTTGGCAGTGATCATGATCTTTGGTAAGAGCTGACCCTGACCTCTGAGCATGGG 840
        etLysThrLeuLeuLeuLeuAlaValIleMetIlePheG

841 GGACAGCCCCAGAAGGGAAGCACTCTTGTCCCTTAGTTTTCTCTCCCATTGCAGTGATCCTCTCTCAGGG 910

911 GGAAAAAAGAAGCCATTTGGGAGGAAGGAGAGTAGCAGAGAGGGGCAGAGAGGGAGGGCACAGAACCCCA 980

3>  981 TGCCCCATCACCAGACAACTCCCAAATTTCCTTCCAGGCCTACTGCAGGCCCATGGGAATTTGGTGAATT 1050
                                                    lyLeuLeuGlnAlaHisGlyAsnLeuValAsnP

3> 1051 TCCACAGAATGATCAAGTTGACGACAGGAAAGGAAGCCGCACTCAGTTATGGCTTCTACGGCTGCCACTG 1120
        heHisArgMetIleLysLeuThrThrGlyLysGluAlaAlaLeuSerTyrGlyPheTyrGlyCysHisCy

3> 1121 TGGCGTGGGTGGCAGAGGATCCCCCAAGGATGCAACGGATCGGTGAGGCCACCTATCCCTCCCTACCCTC 1190
        sGlyValGlyGlyArgGlySerProLysAspAlaThrAspAr

1191 CTAGACTCTGGCCCAGGCAGGGCTGGGAGCTGCAAAGACAGTGCCGGTTCCTGATGGGCGCAGAGGTCTC 1260

1261 AGGATGGCCTGGCTGGAAAAGCAGCCGGCATGTTGGAACTTCTGCTCTAGACTGTTGCAAAGTCACTGGG 1330

1331 TCTCTGCCCAGGGTCCAAGGGGGTGAGACCACAGGCACCAGGCCTCCTGGAGCTGTGGGACAAGAGCCCC 1400

4> 1401 AACAGGTGTCTCCTCACAGCTGCTGTGTCACTCATGACTGTTGCTACAAACGTCTGGAGAAACGTGGATG 1470
                                gCysCysValThrHisAspCysCysTyrLysArgLeuGluLysArgGlyCy

4> 1471 TGGCACCAAATTTCTGAGCTACAAGTTTAGCAACTCGGGGAGCAGAATCACCTGTGGTAAGAGTCCTACC 1540
        sGlyThrLysPheLeuSerTyrLysPheSerAsnSerGlySerArgIleThrCysA

1541 TCACCATCGAGTGGCCCTCATTTGTTTAGACAGTGCTGGGACTGTGCTGGGCACCAAAGATAGACACAGA 1610

1611 GGGACACAGTTCCTGCTTCAGGAAGCTCACGGTTGAGTGGGAAGCCAGGAAAGTGAAAATCCAATGTAGT 1680

1681 AAAGACTCCAGTGGGAAGTAAACAAACAGATAAGGCATTAACACAGCCTGAGGCTTGAGGAAGGCTCCTG 1750

1751 GAAGGGGTGACCCCTAAGCTGAGTCTGAAAGGCTGTGCAGAGAGTCAGGGAAGAGGAGGGAGCATTCCCA 1820

1821 GAAGAGGACACAGCATGGTCAAAGGCACTAAAGGGCACTGTAAGCCATTCTGTACTGCCCAGCAGAAACA 1890

1891 TGAGGAAGAGGAGCAGTGCTGAGCCATGATGCTGGAGACATAGGAAGGAGCTAGGTCAATCCGCCCTCCA 1960

1961 CTCCGGGCTGTATTTAGGTTTTGCCCTAAAGCAATAGGATGCTATTAAGCAAAGGAGCTACAGGGTCAGA 2030

2031 TTTGCATTTTAGATGACTCACTGTGGGGACAGGGTCGATGGAGACAAGTGGAAGGGGCAGAGAAAGCTA 2100

2101 TTGCCATCATGCAGGCAAGAGGGAGTAACATCTTGACATAAAACAATGGAGGTCAGGATGGGAAAGGTGG 2170

2171 AGAAAAAATCAAGATGCATTTGAGATGGAATGCAGCTGAACTGGTGACTGAGTTGGGAGGGATGGGAGA 2240

2241 GGGAGTTGTTGGATGGATATGTGGCTGCATGGATGGCACAACTGTGATAAAGACCATGGGAGCAGGTCAT 2310

2311 GGTGGAGGGTGGGGAGGAGCAGTTCTATTTCCAGCATGTTGAGTTTAGGGGCCTCCAGCACCCAGGGAGG 2380
```

FIG. 7-2

2381 GGTCCAGCAGGCAGCTGTCTATACAAATGCAGCTCAGGGGAGAATTCAGGACTGGGACACAGATTCAGAA 2450
2451 GCCAGCAGCAGAGACCTGAGAGGTGGGTGTGATCACTCATTTGCTGTTTAAAGGCCCAGAAAGGAGACAG 2520
2521 AGAAGGGATGGACAGAGAGGGAGAAGGGGAACTGAGCGAGAAGGTCAAGGAGTCAGTAAGGAAATGGTTA 2590
2591 GCAAGGGCCAAGTGAACAGGGAGTCCTCCATGAAAAGGGCCAACAAGGCTCCCCTGGATGTTGAGGCAGA 2660
2661 AACGCATGAGGGACTCAGGGAAGCTGTTTCCATGGAGTCGGGAGGGCAAAGCCAGATTAGACCAGGTGGG 2730
2731 GGCTGATGGGAAGGCAAATAAAGACAGGAGGCAAAGACAACATTCTGGAGAAAGTTTGGCCTGAAGGGAG 2800
2801 GAGAGTGGTGGCACTGGAAGGCTTTGCTTGGTGTCCCCAGACAGCTGACTCATGAGTGGGATTTGGAAAA 2870
2871 AGCGTGGACTCCTGCCCATGGCCTGAGTCCTTTAAGATCAGAAATTATGTCTCCCATCATGGCCTCTCCA 2940
2941 TAGAGGCATGTATCTTCAGCAGGCGTTAGGTCACAAGCCACATGATGCCAAGCTGACAGTGGCTTGCATA 3010
3011 ATGGGGATATGTGACTGTCGCATAACTAGAATTCTGGAAGAGTGCAGTGCCAGGCTTGGGGCAGCTTTCC 3080
3081 AGCCATGTCATTAAGAATCCAGCCTTCTCCTGGCCTTCAGCTATGCCACGTGGCCAGTGTCTACACCTGG 3150
3151 GATGTCAAGAGACAGGCTGCAGGTCCACCCTCCTGGCCTCATACTATGGAAGAGGCTTTCCTTTTGGGCA 3220
3221 TCTCTCTTTTTGGAGGGAGGAAATAGATCGTTCCCAGAAGCCCCCAGCAGACTTCCCCTTGTTGCTCATT 3290
3291 GGTTGGAACAAGGTTACATGATACACAAAGACCAATCACTGCAAAGGAAAAAGGGATGACCCTGCCTGGC 3360
3361 TTACACCAATCACAATCTATTCCCAGACCCCCCGAGGCTAGGGCTTTGCCTCCTGGACACATCTGTTAGC 3430
3431 AAGAGGAAGAGATTATGGCTGTTAGGAAGGCCTTTGAGAAAGTATCCCAGTGCCTGGCTGTGTCTCCACC 3500
3501 AGGCTGGAGGCCAGCATCCCAAGGGCAAGAATTCTGTCTCCCCATTGGTCAGAAATATCTGGAGCGCAGG 3570
3571 TGTTTGTCTCCAACTAGGAGCTTCTGGAGGACAGGGCTGTGTCTTCTACCCCAGGGTTCCACAAGAAGCC 3640
5>3641 ACTGAATATTAATAAAGTCCCATCTTGTGTTTATTTTCTTATGATTTCAAAACAGGACTCCTGCAGAAGT 3710
                                       laLysGlnAspSerCysArgSer

5>3711 CAACTGTGTGAGTGTGATAAGGCTGCTGCCACCTGTTTTGCTAGAAACAAGACGACCTACAATAAAAAGT 3780
    GlnLeuCysGluCysAspLysAlaAlaAlaThrCysPheAlaArgAsnLysThrThrTyrAsnLysLysT

5>3781 ACCAGTACTATTCCAATAAACACTGCAGAGGGAGCACCCCTCGTTGCTGA... 3830
    yrGlnTyrTyrSerAsnLysHisCysArgGlySerThrProArgCys***

RASF Procaryctic expression vector Construction

N-terminal Hookup:

```
        <EcoRI>                                      <BclI>
VECTOR-->G    AATTCTGGAATTTGGTGAATTTCCACAGAAT              GATCAAGTTG-->RASF
      -->CTTAA    GACCTTAAACCACTTAAAGGTGTCTTACTAG          TTCAAC-->
         (GluPhe) TrpAsnLeuValAsnPheHisArgMetIle           LysLeu
                   +1                                      +11
```

C-terminal hookup:

```
RASF-->CCTCGTTGCTGAGTCCCCTCTTCCCTGGAA          <HindIII>
                                               AGCTT-->VECTOR
       GGAGCAACGACTCAGGGGAGAAGGGACCCTTCGA      A-->
        ProArgCys***
         +124
                                    Mutagenized base (C --> G)------
```

SYNOVIAL PHOSPHOLIPASES

RELATED APPLICATION

This application is a continuation-in-part of Ser. No. 089,883, filed 27 Aug. 1987, now abandoned, the disclosure of which is incorporated by reference herein.

TECHNICAL FIELD

The present invention relates to the isolation, characterization, and production by recombinant means of proteins More particularly, the present invention is related to synovial phospholipase $A_2$.

BACKGROUND

Inflammatory disorders presently account for a significant percentage of debilitating diseases Chronic conditions, such as rheumatoid arthritis, systemic lupus, psoriasis, and possibly atherosclerosis, stem from inflammatory reactions in the joints, skin and blood vessels. It is now apparent that a central role in the inflammatory reaction is the production of phospholipid metabolites called eicosanoids. It is generally accepted that in most tissues the synthesis of the eicosanoids is limited by the availability of arachidonic acid (AA) which is liberated from esterified stores in complex lipids The liberation of AA is accomplished by the activity of phospholipases Phospholipase $A_2$ ($PLA_2$; EC3.1 1.4) catalyzes the release of fatty acids from the $sn^2$ position of 1,2-diacyl-sn-glycero-3-phosphocholines. The best characterized varieties are the digestive enzymes secreted as zymogens in the pancreas of mammals. Amino acid sequences and cDNAs have been cloned for pancreatic $PLA_2$ enzymes from a variety of mammals. See, e.g , O'Hara et al (1976) *J. Biochem.* 99:733-739; Dufton et al. (1983) *Eur. J. Biochem.* 137:537-544; Grataroli et al. (1982) *Eur. J. Biochem.* 122:111-117. These mammalian $PLA_2$ enzymes have a close homology to venom phospholipases of snakes and bees Dufton et al., supra. In particular, the key active site residues and the alignment of cysteines appear to be highly conserved X-ray crystallographic studies of bovine pancreatic $PLA_2$, along with several venom enzymes, have led to the development of detailed models for $PLA_2$ enzyme structure and mechanism of action See, e.g., Renetseder et al. (1985) *J. Biol Chem* 260:11627-11634 Both pancreatic and venom $PLA_2$ have been shown to be proinflammatory. Pruzanski et al. (1986) *J. Invest. Dermatol* 86:380-383. An additional digestive $PLA_2$ has been isolated from pig intestine and a partial amino acid sequence deduced Verger et al (1982) *Biochemistry* 21:6883-6889.

The structure of pancreatic $PLA_2$ has been used as a model for designing novel $PLA_2$ inhibitors. This approach, however, has not led to the design of a drug which has proved effective in inhibiting inflammation in vivo.

If $PLA_2$ plays a central role in mammalian inflammatory disease, however, it probably is not through any of the digestive forms in most instances. Rather, analogous $PLA_2$ enzymes, referred to as "cellular" $PLA_2$ enzymes appear to be the likely regulator of AA release during the onset of inflammation. Unfortunately, these cellular $PLA_2$ enzymes are not well understood This is due to the fact that they are difficult to obtain in quantity and require more extensive purification than the digestive forms of $PLA_2$.

Cellular forms of $PLA_2$ have been isolated from a wide variety of mammalian tissues and cell types, including brain (Gray & Strickland, 1982, *Can. J. Biochim.* 60:108-117), liver (DeWinter et al., 1982, *Biochim. Biophys. Acta* 712:332-341), lung (Franson et al. , 1982, *Lung* 160:275-284; Garcia et al., 1975, *Biochim. Biophys Res. Comm* 64:128-135; Sahu & Lynn, 1977, Biochim. Biophvs. Acta 489:307-317), intestine (Verger et al., 1982, *Biochemistry* 21:6883-6889), spleen (Teramoto et al., 1983, *J. Biochim.* 93:1353-1360), macrophages (Trotter & Smith, 1986, *Neurochem. Res.* 11:349-361; Lanni & Franson, 1981, *Biochim. Biophys. Acta* 658:54-63; Vadas & Hay, 1980, *Life Sciences* 26:1721-1729; Vadas et al., 1981, *Nature* 293:583; Wightman et al., 1981, *Biochim. J.* 200:441-444; Franson et al., 1973, Biochim. Biophys. Acta 296:365-373), leukocytes Traynor & Authi, 1981, *Biochim. Biophys. Acta* 665:571-577; Franson et al., 1977, *Biochim. J.* 167:839-841), erythrocytes (Kramer et al., 1978, *Biochim Biophys. Acta* 507:381-394), ascitic fluid (Forst et al., 1986, *Biochemistry* 25:8381-8385), chondrocytes (Chang et al., 1986, *J. Immunol.* 136:1283-1287), and platelets (Hayakawa et al., 1988 *J. Biochem* 103:263-266; Hayakawa et al., 1987, *J. Biochim.* 101:1311-1314; Jesse & Franson, 1979, *Biochim. Biophys. Acta* 575:467-470; Apitz-Castro et al., 1979, *Biochim. Biophys. Res. Comm.* 91:1, 63-71). For a review, see Van Den Bosch (1980) *Biochim. Biophys Acta* 604:191-246. See also, commonly owned U.S. Pat. application, Ser. No. 946,557, filed 24 Dec. 1986.

Of particular interest is the isolation of a $PLA_2$ from inflammatory exudates, such as the synovial fluid of rheumatoid arthritis patients Stefanski et al., (1986) *J. Biochim.* 100:1297-1303; Vadas et al. (1985) *Life Sciences* 36:579-587; Vadas & Pruzanski (1984) *Adv. Inflammation Res.* 7:51-59; Vadas et al. (1981) *Nature* 293:583-585; Pruzanski et al. (1985) *J. Rheumatol* 12:211-216; Silverman et al., American Rheumatism Ass'n: 51st Annual Scientific Meeting (9-13 June 1987, Washington, D.C.); Pruzanski et al., ibid.

Of these various cellular enzymes, the reports of their activity differ in size, pH optima, substrate specificity, $Ca^{++}$ requirement, form (soluble vs. membrane-associated), and abundance. Since no complete protein sequences have been publicly reported for these isolates (partial sequences published by Verger et al., 1987, supra; and Hayakawa et al., 1988 supra), it is difficult to say which, if any, of these isolates represent the same enzymes. Moreover, it is difficult to completely discriminate between $PLA_1$ and $PLA_2$ directly in all but highly purified isolates, since cleavage at the $sn^2$ position of phospholipids can also be the result from the combined sequential activities of $PLA_1$ and lysophospholipase. As can be seen, however, many of these enzymes have been prepared from cells associated with inflammatory responses (i.e., macrophages, leukocytes, chondrocytes, synoviocytes, etc.) or inflammatory exudates. Nevertheless, the lack of cause/effect data has made it difficult to establish which, if any, of these enzymes are key in the inflammatory response.

The isolation of the $PLA_2$ form responsible for rheumatoid arthritis in vivo would provide an important tool useful in the design of anti-inflammatory drugs Based on the work with digestive and venom $PLA_2$ inhibitors, it is believed that the form(s) of $PLA_2$ responsible for inflammatory disease, while similar, are sufficiently different in structure such that inhibitors of digestive or venom $PLA_2$ do not necessarily inhibit the latter form in vivo Thus, to efficiently design specific inhibitors, it is necessary to isolate the specific PLA$_2$(s) that are involved in rheumatoid arthritis in sufficient quantity so that it can be structurally characterized. PLA$_2$ is also generally useful in the food processing industry (Dutilh & Groger, 1981, *J. Sci. Food Agric.* 32:451–458) and the preservation of fish. Mazeaud & Bilinski (1976) *J. Fish Res. Board Can.* 33:1297–1302.

SUMMARY OF THE INVENTION

According to the present invention, it has been discovered that a new family of mammalian phospholipase A$_2$, hereinafter referred to as synovial phospholipases A$_2$ (synovial PLA$_2$ or sPLA$_2$), are encoded within the mammalian genome, and are substantially different from the known PLA$_2$ enzymes in both DNA and amino acid sequences. The cloning of the genes for sPLA$_2$ provides for the structural characterization of these new enzymes, as well as methods of producing them in substantial and purified quantities. Thus, the present invention provides, inter alia, an important tool useful in the design of anti-inflammatory drugs.

In one embodiment, the present invention provides a composition containing double-stranded DNA construct comprising a heterologous region, said region comprising a coding sequence for a mammalian synovial phospholipase A$_2$, said composition being substantially free of constructs that do not contain said heterologous region. This DNA construct may or may not be contained within a replicon.

In another embodiment, the present invention provides a method of producing a recombinant mammalian synovial phospholipase A$_2$ comprising: providing a population of transformed cells comprising a replicon functional in said cells, said replicon comprising a coding sequence under the control of a promoter functional in said cells, said coding sequence encoding a mammalian synovial phospholipase A$_2$, said population being substantially free of other cells; growing said population under conditions whereby said mammalian synovial phospholipase A$_2$ is expressed; and recovering said mammalian synovial phospholipase A$_2$. The method of the present invention can employ any suitable procaryotic or eucaryotic expression system.

In a further embodiment, the present invention provides a composition comprising mammalian synovial phospholipase A$_2$ substantially free of contaminating proteins.

In still another embodiment, the present invention provides anti-mammalian synovial phospholipase A$_2$ antibody, and methods of treating inflammatory disorders employing anti-mammalian synovial phospholipase A$_2$ antibodies.

DESCRIPTION OF THE FIGURES

FIG. 1 shows a comparison between the N-terminal amino acid sequences of synovial phospholipases of the present invention and other phospholipases. hRASF-Peak A and Peak-B are two synovial PLA$_2$s isolated from human synovial fluid NP is the "non-pancreatic" type of PLA$_2$ described in copending U.S. Pat. application, Ser. No. 946,557, including the human (h), porcine (p) and rat (r) forms. The sequence designated "h cln 10" is derived from clone λSPLA2-10 (FIG. 4) and may be an spLA$_2$ type B or C sequence or a different PLA$_2$. Also shown in the figure are several pancreatic PLA$_2$s: porcine intestinal PLA$_2$ (p Intestine), rabbit ascites PLA$_2$ (rab Ascites), rat platelet PLA$_2$ (r platelet); and two snake venoms: *Crotalus atrox* (*C. atrox*), and *Agkistrodon piscivorus* (A. pisc K-49).

FIG. 3 shows the DNA sequence of two 50-mer oligonucleotide probes used to identify synovial PLA$_2$ clones.

FIG. 4 shows the DNA sequences of two human PLA$_2$ genomic clones, λSPLA2-6, and λSPLA2-10, which contain exons of the two PLA$_2$ enzymes described herein.

FIG. 5 shows a 60-mer oligonucleotide probe synthesized to match amino acid residues 5-24 of sPLA$_2$ type A shown in FIG. 1 and based on the nucleotide sequence of clone λsPLA2-6.

FIG. 6 shows the nucleotide sequence and deduced amino acid sequence from a cDNA clone for human sPLA$_2$ type A, designated λSPLA2cDNA-4.

FIG. 7 shows the nucleotide sequence of xons 1-5 from genomic clone λSPLA2-6 of human sPLA$_2$ type A.

FIG. 8 shows oligonucleotide linkers useful in recombinant DNA constructs for the expression of sPLA$_2$ in *E. coli.*

DETAILED DESCRIPTION

Figure 2:
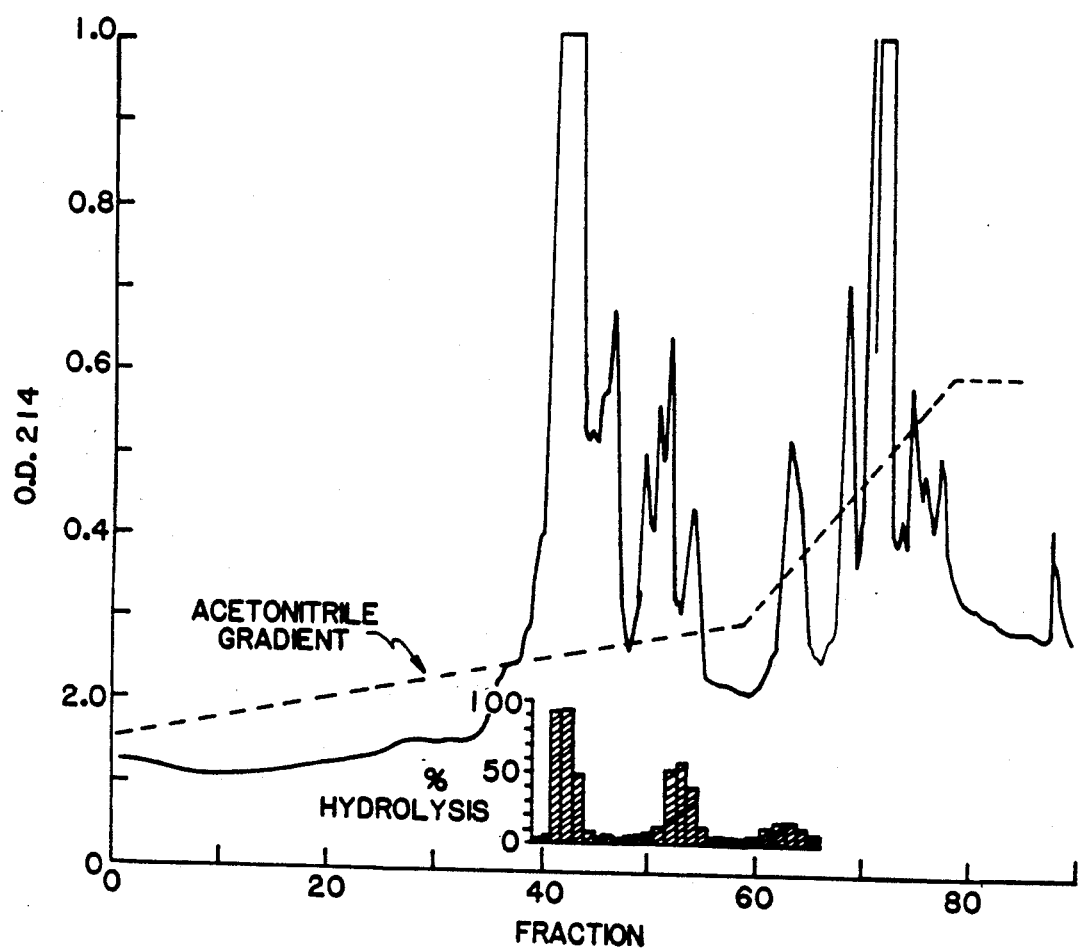
FIG. 2 is a C$_4$ reverse phase HPLC profile of partially purified synovial PLA$_2$ showing the enzyme activity and optical density profile.

The practice of the present invention will employ, unless otherwise indicated, conventional molecular biology, microbiology, and recombinant DNA techniques within the skill of the art. Such techniques are explained fully in the literature. See e.g., Maniatis, Fritsch & Sambrook, MOLECULAR CLONING: A LABORATORY MANUAL (1982); DNA CLONING: A PRACTICAL APPROACH, Volumes I and II (D.N. Glover ed. 1985); GONUCLEOTIDE SYNTHESIS (M.J. Gait ed. 1984); NUCLEIC ACID HYBRIDIZATION (B.D. Hames & S.J. Higgins eds. 1985); TRANSCRIPTION AND TRANSLATION (B.D. Hames & S.J. Higgins eds. 1984); ANIMAL CELL CULTURE (R.I. Freshney ed. 1986); IMMOBILIZED CELLS AND ENZYMES (IRL Press, 1986); B. Perbal, A PRACTICAL GUIDE TO MOLECULAR CLONING (1984).

In describing the present invention, the following terminology will be used in accordance with the definitions set out below.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A polyadenylation signal and transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the translation start codon of a coding sequence and extends upstream (5' direction) to include the minimum number of bases or elements necessary to initiate transcription at levels detectable above background Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the −10 and −35 consensus sequences.

A coding sequence is "under the control" of the promoter sequence in a cell when RNA polymerase which binds the promoter sequence transcribes the coding sequence into mRNA which is then in turn translated into the protein encoded by the coding sequence.

A cell has been "transformed" by exogenous DNA when such exogenous DNA has been introduced inside the cell wall. Exogenous DNA may or may not be integrated (covalently linked) to chromosomal DNA making up the genome of the cell. In procaryotes and yeast, for example, the exogenous DNA may be maintained on an episomal element such as a plasmid. With respect to eucaryotic cells, a stably transformed cell is one in which the exogenous DNA has become integrated into a chromosome so that it is inherited by daughter cells through chromosome replication. This stability is demonstrated by the ability of the eucaryotic cell to establish cell lines or clones comprised of a population of daughter cells containing the exogenous DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 85% (preferably at least about 90%, and most preferably at least about 95%) of the nucleotides match over the defined length of the DNA sequences. Sequences that are substantially homologous can be identified in a Southern hybridization experiment under, for example, stringent conditions as defined for that particular system. Defining appropriate hybridization conditions is within the skill of the art. See, e.g., Maniatis et al., supra; DNA CLONING, Vols. I & II, supra: NUCLEIC ACID HYBRIDIZATION, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally occurring mutational events do not give rise to a heterologous region of DNA as defined herein.

A protein composition is "substantially free of contaminating proteins" when at least about 75% by weight of the protein in the composition is the particular protein of interest. Preferably, this protein comprises at least about 90% by weight of the protein in the composition, most preferably at least about 99% by weight. It is also preferred that a protein composition, which is substantially free of contaminating proteins, contain only a single molecular weight species having the activity of the protein of interest.

"Synovial phospholipase $A_2$" (synovial $PLA_2$ or $sPLA_2$) refers to the class of mammalian enzymes exhibiting $PLA_2$ activity and found in the synovial fluid of a mammal (such as a human) afflicted with rheumatoid arthritis. It is believed that $sPLA_2$ enzymes are produced by inflamed synovial tissue, or perhaps granulocytes or macrophages in the synovial fluid. $PLA_2$ enzymes are characterized in having a molecular weight of about $15+3$ kD when measured by polyacrylamide gel electrophoresis (PAGE) (12.5% polyacrylamide gel, 0.1% SDS). Representative of the family of enzyme are $sPLA_2$ type A, type B and type C. The $NH_2$-terminal amino acid sequence of types A and B are shown in FIG. 1. The complete amino acid sequence of type A, deduced from the human cDNA clone $\lambda PLA_2 cDNA$-4, is shown in FIG. 6. Type A is present in synovial fluid from all types of arthritis examined. Type B varies in abundance from complete absence in some rheumatoid samples to about 33% of the total activity in other samples. Type B typically appears at higher levels in fluid samples from osteoarthritis patients than in samples from rheumatoid patient, but type A still constitutes the majority of $sPLA_2$. Type B also shows considerable stimulation in hydrolytic activity relative to type A in the presence of either 0.5 M Tris or 0.1% Na deoxycholate; type A is inhibited by 0.5 M Tris. Type C, when present, is two- to five-fold less abundant than type B. These extracellular enzymes are (i) soluble, (ii) calcium-dependent, (iii) have proinflammatory activity in tissue when injected intradermally or intraarticularly, and (iv) exhibit absolute specificity for the sn-2 acylester bond of dipalmitoylphosphatidylcholine. This characterization also includes synthetic and recombinant analogs of $sPLA_2$ wherein any resulting changes, deletions or additions in the amino acid sequence does not change the above characteristic activities.

The sequences compared in FIG. 1 show that $sPLA_2$ resembles other $PLA_2$ sequences in the number and placement of the 14 Cys residues, particularly the "type II" enzymes, of which *C. atrox* PLA$_2$ is an example. Synovial PLA$_2$ also lacks a Cys at position 11, which is characteristic of the highly pro-inflammatory type II enzymes (e.g., Viperid snake venom forms, and PLA$_2$ species described in copending U.S. Ser. No. 946,557). The comparison demonstrates that sPLA$_2$ is distinct from all other known PLA$_2$ sequences, particularly in the variable regions near the carboxy terminus. A twenty residue prepeptide, containing a typical signal for translocation across a cellular membrane is present upstream of the mature enzyme sequence, and is presumably cleaved during or after synthesis.

A clone, λSPLA2-6, of genomic DNA encoding sPLA$_2$ type A has been deposited with the American Type Culture Collection (ATCC), 12301 Parklawn Dr., Rockville, MD, U.S.A. 20852, on 14 Aug. 1987, and given accession no. 40361. The coding sequence (FIG. 4) is on a 404 bp AluI fragment which can be isolated from λSPLA2-6. An additional clone, which may represent a human genomic sequence from at least one exon of sPLA$_2$ type B or C, and called λSPLA2-10, was also deposited on 14 Aug. 1987 with the ATCC under accession no. 40360. The coding sequence in this clone is contained on an AluI fragment of about 460 bp. A cDNA clone encoding all of human sPLA$_2$ type A on an 854 bp EcoRI fragment, designated λSPLA2cDNA-4, was deposited with the ATCC on 27 May 1988 under accession no. 40456. An expression vector containing an sPLA$_2$ coding sequence, p86-1A (discussed below), was also deposited with the ATCC on June 27, 1988 under accession no. 67735. These deposits will be maintained under the terms of the Budapest Treaty. The sPLA$_2$ coding sequences of λSPLA2-6, λSPLA2-10 and λSPLA2cDNA-4, and the expression cassette sequence of pHNF86 are incorporated herein by reference. In the event of any discrepancy between a sequence disclosed herein and the sequence of a deposited clone, the clone's sequence is controlling.

While it is possible to purify sPLA$_2$ from an appropriate tissue/fluid source (see below), it is preferred to produce it by recombinant methods. A DNA sequence encoding sPLA$_2$ can be isolated by one of several approaches. These methods will rely in part on nucleic acid hybridization using appropriate oligonucleotide probes. Such probes can be constructed synthetically based on the sPLA$_2$ DNA or amino acid sequences disclosed herein, or isolated from the genomic sPLA$_2$ clones also described herein.

The basic strategies for preparing oligonucleotide probes and DNA libraries, as well as their screening by nucleic acid hybridization, are well known to those of ordinary skill in the art. See, e.g., DNA CLONING: VOL. I (D.P. Glover ed. 1985); NUCLEIC ACID HYBRIDIZATION (B.D. Hames & S.J. Higgins eds. 1985); OLIGONUCLEOTIDE SYNTHESIS (M.J. Gate ed. 1984); T. Maniatis et al., MOLECULAR CLONING:A LABORATORY MANUAL (1982); B. Perbal, A PRACTICAL GUIDE TO MOLECULAR CLONING (1984). First, a DNA library is prepared. The library can consist of a genomic DNA library from a selected mammal, such as a human. Human genomic libraries are known in the art. See, e.g., Maniatis et al. (1978) Cell 15:687–701; Lawn et al. (1978) Cell 15:1157–1174. DNA libraries can also be constructed of cDNA prepared from poly-A RNA (mRNA) by reverse transcription. See, e.g., U.S. Pat. Nos. 4,446,325; 4,440,859; 4,433,140; 4,431,7400; 4,370,417; 4,363,877. The mRNA is isolated from a cell line or tissue believed to express sPLA$_2$, such as synovial tissue or inflammatory cells isolated from synovial fluid. The preferred source of mRNA for cDNA library constructions is synovial joint tissue. The genomic DNA or cDNA is cloned into a vector suitable for construction of a library A preferred vector is a bacteriophage vector, such as any of the phage lambda. The construction of an appropriate library is within the skill of the art. See, e.q., B. Perbal, supra.

Once the library is constructed, oligonucleotides are used to probe the library to identify the segment carrying the sPLA$_2$ coding sequence. In general, the probes are preferably based upon known nucleic acid sequences. However, if the later is unknown, it may be desirable to base probes upon an amino acid sequence determined from a purified sPLA$_2$. In the latter case, nucleotide sequences are selected so as to correspond to the codons encoding the amino acid sequence. Since the genetic code is redundant, it will usually be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate. It may not be necessary, however, to prepare probes containing codons whose usage is rare in the mammal from which the library was prepared.

In certain circumstances, one of skill in the art may find it desirable to prepare probes that are fairly long and/or encompass regions of the amino acid sequence which would have a high degree of redundancy in the corresponding nucleic acid sequences. Probes covering the complete gene, or a substantial part of the gene, may also be appropriate, depending upon the expected degree of homology. Due to the highly conserved nature of PLA$_2$ across species lines, it is likely that full length sPLA2cDNA probes from one species, such as the human clone λSPLA2cDNA-4, can be readily used to screen libraries prepared from another species. In other cases, it may be desirable to use two sets of probes simultaneously, each to a different region of the gene. While the exact length of any probe employed is not critical, generally it is recognized in the art that probes from about 14 to about 20 base pairs are usually effective. Longer probes of about 25 to about 60 base pairs are also used.

As is known in the art, oligonucleotide probes are labeled with a marker, such as a radionucleotide or biotin, using standard procedures. The labeled set of probes is then used in the screening step, which consists of allowing the single-stranded probe to hybridize to isolated ssDNA from the library, according to standard techniques. Either stringent or permissive hybridization conditions could be appropriate, depending upon several factors including, but not limited to, the length of the probe, whether the probe and library are from the same species, and whether the species are evolutionarily close or distant. It is within the skill of the art to optimize hybridization conditions so that homologous sequences are isolated and detectable above background hybridizations. The basic requirement is that hybridization conditions be of sufficient stringency so that selective hybridization occurs; i.e., hybridization is due to a minimum degree of nucleic acid homology (e.g., at least about 75%), as opposed to nonspecific binding or hybridization due to a lower degree of homology. See generally, NUCLEIC ACID HYBRIDIZATION, supra. Once a clone from the screened library has been identified by positive hybridization, it can be further characterized by restriction enzyme analysis and DNA sequencing to confirm that the particular clone contains a coding sequence for sPLA$_2$.

Partial genomic clones, such as the clone of an exon of sPLA$_2$ in λSPLA2-10, can be extended into complete clones by one of several techniques. A clone can be extended in either the 5' or 3' direction using "chromosome walking" techniques to ensure inclusion of the entire gene coding region. Restriction fragments of these clones can then be probed with, for example, sPLA$_2$ DNA. If sufficient homology exists within these exons to pancreatic PLA$_2$, other exons of sPLA$_2$ could be identified with pancreatic sPLA$_2$ clone, also. When using non-sPLA$_2$ cDNA probes, it is particularly preferred to probe with oligonucleotides which correspond to particularly conserved regions (e.g., amino acid residues 44–52), which would allow prediction of possible differences (e.g., Asp$_{49}$ changed to Lys$_{49}$).

Other coding regions in genomic clones may be rapidly identified by direct sequencing of the DNA downstream of a cloned exon using modern M13-dideoxy sequencing techniques. The sequence is then inspected in all three reading frames to reveal an open reading frame. Other exons will also be apparent since they will be bounded on both sides by intron-splicing signals and should encode conserved amino acids.

More specifically, now that the correct gene coding sequence for an exon of sPLA$_2$ type B or C is known, it can be used to obtain the entire protein coding region of the enzyme by one or more of the following means. First, the exon can be trimmed from the λ clone and placed in a more convenient vector, such as pBR322, so that large quantities of DNA containing only the exon itself can be obtained and used as a hybridization probe. Alternately, a 60-mer oligonucleotide corresponding to the unique regions of the coding region (e.g., amino acid residues 6–25) can be synthesized. Either can be used as a hybridization probe for northern blots of mRNA obtained from various sources, such as, peritoneal cells and pus, endothelial tissue, and peripheral blood leukocytes, lymphocytes, and macrophages In addition, mRNA from various cell lines such as differentiated U-937 and HL60 can also be tested. Any tissue or cell source containing detectable levels of hybridizing mRNA is then used to produce a cDNA library which will then be screened with the same probes in order to detect a full-length cDNA encoding sPLA$_2$. Indeed, as described below, this strategy lead to the cloning of full length cDNA's encoding sPLA type A, such as clone λSPLA2cDNA-4.

Alternately, in the absence of a good tissue source for the mRNA, it may become necessary to obtain internal sequences from the type B or C protein. This can be done, for example, by Staph-V8 proteolysis of peak A material purified in the usual way (described below), followed by reductive alkylation and separation by HPLC of the digestion products. Elution peaks corresponding to discrete enzyme fragments can then be sequenced as before. Alternatively, putative amino acid sequences from cDNA clones can be employed. From the resulting sequence, oligonucleotides can be designed and produced for use as hybridization probes to locate the other exons. Ultimately, the isolated exons are ligated together in such a way that the correct mature protein is encoded.

Mammalian genomic clones (partial or full-length) containing the longest inserts of the sPLA$_2$ gene can be co-transfected into Chinese hamster ovary (CHO) cells with plasmid DNA containing a marker, such as neomycin and metallothionine resistance genes. Surviving cells selected in the presence of antibiotic G418 and Cd$^{++}$, and surviving clones can be analyzed for the presence of sPLA$_2$-hybridizing transcripts in a Northern blot of extracted RNA. Clones containing the desired transcripts can then be used as an mRNA source for a cDNA library construction. Synovial PLA$_2$ can be purified from human synovial fluid from patients afflicted with rheumatoid arthritis or psoriasis. The purification protocols, described in detail below, allow for the first time the purification of native sPLA$_2$ in sufficient quantity and at a high enough purity to permit accurate amino acid sequencing. The amino acid sequences derived from the purified sPLA2's allow for the design of probes to aid in the isolation of native sPLA$_2$ nucleic acid sequence, or the design of synthetic nucleic acid sequences encoding the amino acid sequence of a sPLA$_2$.

Specific anti-sera or monoclonal antibodies (described below) can be made to a synthetic sPLA$_2$ peptide having the sequence of amino acid residues, such as those shown at the NH$_2$-terminus in FIG. 1. Particularly preferred is a peptide spanning positions 1 through 26. This is a unique region of the protein, and antibodies thereto can be used to immunoprecipitate any sPLA$_2$ present in a selected tissue, cell extract, or body fluid. Purified sPLA$_2$ from this source can then be sequenced and used as a basis for designing specific probes as described above. Antibodies to other regions that diverge from known PLA$_2$s can also be used. Also useful as antigens are purified native or recombinant sPLA$_2$.

As mentioned above, a DNA sequence encoding sPLA$_2$ can be prepared synthetically rather than cloned. The DNA sequence can be designed with the appropriate codons for the sPLA$_2$ amino acid sequence. In general, one will select preferred codons for the intended host if the sequence will be used for expression. The complete sequence is assembled from overlapping oligonucleotides prepared by standard methods and assembled into a complete coding sequence. See. e.q., Edge (1981) Nature 292:756; Nambair et al. (1984) Science 223:1299; Jay et al. (1984) J. Biol. Chem. 259:6311.

Synthetic DNA sequences allow convenient construction of genes which will express sPLA$_2$ analogs or "muteins". Alternatively, DNA encoding muteins can be made by site-directed mutagenesis of native sPLA$_2$ genes or cDNAs, and muteins can be made directly using conventional polypeptide synthesis. Of particular interest in the construction of muteins is changing the catalytic His$_{48}$ residue in type A to another amino acid, such as Gln. Position 48 muteins may act as a PLA$_2$ inhibitor by binding to endogenous inflammatory PLA$_2$ enzymes, thereby creating inactive dimers. Other potential targets for mutagenic alteration include the three basic residues near the N-terminus (positions 7, 10 and 16), which may be involved in interaction with membrane-associated substrates. Muteins altered in any one or all of these positions by the substitution of acidic residues (e.g., Glu or Asp) could have reduced activity toward membrane-bound or complex substrates.

Site-directed mutagenesis is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

Once a coding sequence for sPLA$_2$ has been prepared or isolated, it can be cloned into any suitable vector or replicon and thereby maintained in a composition which is substantially free of vectors that do not contain an sPLA$_2$ coding sequence (e.g., free of other library clones). Numerous cloning vectors are known to those of skill in the art, and the selection of an appropriate cloning vector is a matter of choice. Examples of recombinant DNA vectors for cloning and host cells which they can transform include the various bacteriophage lambda vectors (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), actinophage, φC31 (Streptomyces), YIp5 (Saccharomyces), YCp19 (Saccharomyces), and bovine papilloma virus (mammalian cells). See generally, DNA CLONING:VOLS. I & II, supra; T. Maniatis et al., supra; B. Perbal, supra.

According to the present invention, the coding sequence for mammalian sPLA$_2$ is placed under the control of a promoter, ribosome binding site (for bacterial expression) and, optionally, an operator (collectively referred to herein as "control" elements), so that the DNA sequence encoding sPLA$_2$ is transcribed into RNA in the host cell transformed by a vector containing this expression construction. The coding sequence may or may not contain a signal peptide or leader sequence. If the coding sequence contains a signal peptide, it may or may not be the sPLA$_2$ signal sequence. In bacteria for example, mature sPLA$_2$ is preferably made by the expression of a coding sequence which does not contain the sPLA$_2$ signal peptide, or by expression of a coding sequence containing a leader sequence which is removed by the bacterial host in post-translational processing. See. e.q., U.S. Pat. Nos. 4,431,739; 4,425,437; 4,338,397.

An expression vector is constructed according to the present invention so that the sPLA$_2$ coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). The control sequences may be ligated to the coding sequence prior to insertion into a vector, such as the cloning vectors described above. Alternatively, the coding sequence can be cloned directly into an expression vector which already contains the control sequences and an appropriate restriction site. For expression of sPLA$_2$ in procaryotes and yeast, the control sequences will necessarily be heterologous to the coding sequence. If the host cell is a procaryote, it is also necessary that the coding sequence be free of introns (e.g., cDNA). If the selected host cell is a mammalian cell, the control sequences can be heterologous or homologous to the sPLA$_2$ coding sequence, and the coding sequence can either be genomic DNA containing introns or cDNA. Either genomic or cDNA coding sequences can be expressed in yeast.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U. K. Pub. Nos. GB 2,121,054; GB 2,008,123; GB 2,007,675; and European Pub. No. 103,395. Preferred procaryotic expression systems are in *E. coli*. Other preferred expression vectors are those for use in eucaryotic systems. See, e.g., commonly owned U.S. Pat. application Ser. No. 809,163, filed 16 Dec. 1985, the disclosure of which is incorporated herein. A preferred eucaryotic expression system is that employing vaccinia virus, which is well-known in the art. See, e.g., Mackett et al. (1984) J. Virol. 49:857; DNA CLONING, Vol. II, pp. 191–211, supra: PCT Pub. No. WO 86/07593. Yeast expression vectors are known in the art. See, e.g., U.S. Pat. Nos. 4,446,235; 4,443,539; 4,430,428; see also European Pub. Nos. 103,409; 100,561; 96,491. Another preferred expression system is vector pHS1, which transforms Chinese hamster ovary cells. The use of the vector is described in PCT Pub. No. WO 87/02062 and commonly owned U.S. Pat. application Ser. No. 804,692, filed 4 Dec. 1985, the disclosure of which is incorporated herein by reference.

Depending on the expression system and host selected, sPLA$_2$ is produced by growing host cells transformed by an expression vector described above under conditions whereby the sPLA$_2$ protein is expressed. The enzyme protein is then isolated from the host cells and purified. If the expression system secretes the enzyme into growth media, the protein can be purified directly from cell-free media. If the sPLA$_2$ protein is not secreted, it is isolated from cell lysates. The selection of the appropriate growth conditions and recovery methods are within the skill of the art.

Native, recombinant or synthetic sPLA$_2$ peptides (full length or subunits) can be used to produce both polyclonal and monoclonal antibodies. If polyclonal antibodies are desired, purified sPLA$_2$ peptide is used to immunize a selected mammal (e.g., mouse, rabbit, goat, horse, etc.) and serum from the immunized animal later collected and treated according to known procedures. Compositions containing polyclonal antibodies to a variety of antigens in addition to sPLA$_2$ can be made substantially free of antibodies which are not anti-sPLA$_2$ by immunoaffinity chromatography.

Monoclonal anti-sPLA$_2$ antibodies can also be readily produced by one skilled in the art from the disclosure herein. The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., HYBRIDOMA TECHNIQUES (1980); Hammerling et al., MONOCLONAL ANTIBODIES AND T-CELL HYBRIDOMAS (1981); Kennett et al., MONOCLONAL ANTIBODIES (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against sPLA$_2$ peptides can be screened for various properties; i.e., isotype, epitope, affinity, etc. Of particular interest are monoclonal antibodies that neutralize the activity of sPLA$_2$. Such monoclonals can be readily identified in PLA$_2$ activity assays. High affinity antibodies are also useful in immunoaffinity purification of native or recombinant sPLA$_2$.

The discovery of pancreatic PLA$_2$ expressed in human lung tissue indicates that the pancreatic form may play a larger role than had been expected in inflammatory disease. Thus, antibodies to any other PLA$_2$ forms described herein (both polyclonal and monoclonal) can be used to treat inflammatory disorders. Anti-pancreatic PLA$_2$ antibody can be produced as described herein for anti-sPLA$_2$ antibody. If the disease is acute endotoxic shock, for example, the appropriate therapeutic method would be to treat the patient with an effective dose of anti-PLA$_2$ antibodies (e.g., anti-synovial PLA$_2$) through a conventional intravenous route. In the treatment of local, acute inflammation, treatment with anti-sPLA$_2$ antibody would be indicated, perhaps by intramuscular injection. It is particularly preferred to treat local, chronic inflammation, such as joints of rheumatoid arthritis patients, by parenteral administration of anti-sPLA$_2$ antibody. These compositions may also be useful in treating other forms of arthritis, such as osteoarthritis. Since endotoxic shock induces elevated levels of PLA$_2$, it may also be desirable to administer anti-PLA$_2$ antibodies in conjunction with other therapies directed to the gram-negative pathogens and their toxins (e.g., anti-LPS therapy). Since PLA$_2$ is also known to attack the pulmonary surfactant monolayer, in the case of respiratory distress (e.g., adult respiratory distress syndrome) it may be desirable to administer anti-PLA$_2$ antibodies by inhalation combined with replacement pulmonary surfactant phospholipid, dipalmitoyl phosphatidylcholine. PLA$_2$ antagonists, such as sPLA$_2$ muteins, could also be used in place of antibodies.

The determination of the appropriate treatment regimen (i.e., dosage, frequency of administration, systemic vs. local, etc.) is within the skill of the art. For administration, the antibodies will be formulated in a unit dosage injectable form (solution, suspension, emulsion, etc.) in association with a pharmaceutically acceptable parenteral vehicle. Such vehicles are usually nontoxic and nontherapeutic. Examples of such vehicles are water, saline, Ringer's solution, dextrose solution, and Hank's solution. Nonaqueous vehicles such as fixed oils and ethyl oleate may also be used. A preferred vehicle is 5% (w/w) human albumin in saline. The vehicle may contain minor amounts of additives, such as substances that enhance isotonicity and chemical stability, e.g., buffers and preservatives. The antibody is typically formulated in such vehicles at concentrations of about 1 $\mu$g/ml to 10 mg/ml.

Anti-sPLA$_2$ antibodies will also be useful in diagnostic applications. For example, synovial fluid isolated from rheumatoid arthritis patients shows that it contains primarily, if not completely, PLA$_2$ of the type A variety. On the other hand, samples from osteoarthritis patients typically contain appreciable amounts of type B as well as type A, usually in a 2:1 ratio of type A to type B based upon activity in the presence of 50 mM Tris. Thus, the present invention contemplates a method, particularly a diagnostic method, in which a synovial fluid sample from a human (or other mammal) is provided, and the amounts of sPLA$_2$ type A and type B are quantitatively measured in an assay and compared For example, employing anti-sPLA$_2$ antibodies specific to type A or to type B in a quantitative immunoassay could be used to distinguish between the two types of arthritis. Antibody specific for type A or type B could be formulated into any conventional immunoassay format; e.g., homogeneous or heterogeneous, radioimmunoassay or ELISA. The various formats are well known to those skilled in the art. See, e.g., IMMUNOASSAY: A PRACTICAL GUIDE (D.W. Chan and M.T. Perlstein eds. 1987) the disclosure of which is incorporated herein by reference. Quantitative assays other than immunoassays could also be used to measure the relative levels of type A and type B sPLA$_2$.

In general, recombinant production of sPLA$_2$ can provide compositions of that enzyme substantially free of contaminating proteins. The ability to obtain high levels of purity is a result of recombinant expression systems which can produce sPLA$_2$ in substantial quantities vis-a-vis in vivo sources. Thus, by applying conventional techniques to recombinant cultures, sPLA$_2$ compositions can be produced that are substantially more pure than the cellular PLA$_2$ compositions presently available from non-digestive and non-venom sources.

The purified sPLA$_2$ compositions of the present invention are useful in several regards. First, they can be used in food processing technology as described in Dutilh & Greger (1981) *J. Sci. Food Agric.* 32:451–458. In addition, sPLA$_2$ compositions can be used to delay the onset of rancidity in fish. See, e.g., Mazeaud & Bilinski (1976) *J. Fish Res. Board Can.* 333:1297–1302.

Purified sPLA$_2$, however, will be particularly useful as a tool in the design and screening of inflammation inhibitors. First, milligram amounts of the material are obtainable according to the present invention. Milligram amounts are capable of crystallization to permit three dimensional studies using X-ray diffraction and computer analysis. This may permit deduction concerning the shape of the molecule, thus defining proper shapes for substances useable as inhibitors of the enzyme activity normally exhibited by sPLA$_2$. Inhibitors have already been designed for "converting enzyme", the catalyst for the subsequent conversion of angiotensin I into angiotensin II. Generally, these antagonists have been "dipeptides" whose interactions with converting enzyme are stabilized by modification of the "residues" participating in the peptide bond so as to enhance the ability of the "dipeptide" to interact specifically with converting enzyme. Thus the peptide bond joins specifically chosen carboxylic acids and amines (not necessarily amino acids). These "dipeptides" are configured in a three dimensional array so as to complement the contours of the intended target, converting enzyme. A similar lock and key spatial arrangement may result from molecules designed complementary to the surface contours of the crystallized sPLA$_2$ of the invention. It is understood that "surface" includes convolutions which may face inward, and specifically includes the active site. Furthermore, "complementary" is understood to mean that, in addition to spatial conformations which "fit", interactions between the protein and the molecule which matches its surface contours are attractive and positive. These interactions may be hydrogen bonding, ionic, or hydrophobic affinity.

Accordingly, the invention contemplates peptide antagonists (2-15 amino acids) to sPLA$_2$ which are characterized by three dimensional contours complementary to the three dimensional contours on the surface of recombinant sPLA$_2$. By peptide in this context is meant that the antagonist contains carboxylic acid amide bonds corresponding to one less than the number of residues. The carboxylic acid and amine participants need not be α-amino acids.

Second, even without the assistance of a three dimensional structure determination, purified sPLA$_2$ of the invention is of significance as a reagent in screening sPLA$_2$ inhibitors in vitro as an ad hoc approach to evaluation. Impure sPLA$_2$ preparations currently available yield confusing data due to the impact of the impurities on the test results. For example, contaminants which turn out to be themselves inhibitors, activators, or substrates for sPLA$_2$ will interfere with the evaluation. Thus, a substantial improvement in current screening techniques for sPLA$_2$ inhibitors would be effected by the availability of the purified human sPLA$_2$ protein.

The sPLA$_2$ compositions described herein may also be useful as an anti-cancer drug. For example, direct injection of sPLA$_2$ into, or in the vicinity of malignant tumors, and optionally in conjunction with tumor excision, will result in high levels of powerful chemoattractants for, and activators of, macrophages. These activated macrophages may then enhance localized tumor reduction or elimination.

Still another application of purified sPLA$_2$ according to the present invention is as an adjuvant in a vaccine composition. The formulation of vaccines is well known in the art. Usually, vaccine formulations include the antigen(s) (e.g., attenuated virus, killed virus, viral polypeptide subunits, killed bacteria, bacterial pili, etc.) in a pharmaceutically acceptable parenteral vehicle. The improved vaccine composition of the present invention may contain, in addition to an SPLA$_2$ adjuvant, an additional adjuvant. The concentration of sPLA$_2$ in the final vaccine formulations can be readily determined by one of ordinary skill in the art. Typically, but not always, the concentration of sPLA$_2$ will be from about 1 ng/ml to about 1 μg/ml.

Described below are examples of the present invention which are provided only for illustrative purposes. They are not intended to limit the scope of the present invention in any way as numerous embodiments within the scope of the claims will be apparent to those of ordinary skill in the art in light of the present disclosure. Those of ordinary skill in the art are presumed to be familiar (or to have ready access to) the references cited in the application, and the disclosures thereof are incorporated by reference herein.

EXAMPLES

I. Purification and sequencing of sPLA$_2$

A. Initial purification

Sephadex G-75, CM-Sephadex C-50, and protein standards for gel filtration and electrophoresis were purchased from Pharmacia Fine Chemicals. Acrylamide, N,N,N',N'-tetramethylethylenediamine, bromophenol blue, Coomassie brilliant blue R, sodium dodecyl sulfate (SDS), fatty acid free bovine serum albumin (BSA), dipalmitoylphosphatidylcholine, and Lowry protein assay kit were obtained from Sigma. Silver stain and Bio-Rad protein assay kit were purchased from Bio-Rad Laboratories.

1-[$^{14}$C]Oleic acid (50 mCi/mmol) was purchased from New England Nuclear. 2-[I-$^{14}$C]-palmitoyl-1-palmitoylphosphatidylcholine (59 mCi/mmol) and 2-[1-$^{14}$C]linoleoylphosphatidylethanolamine was supplied by Avanti Polar Lipids (Birmingham, AL). Ampholine PAG plate, pH 3.5-9.5, for analytical electrofocusing was purchased from LKB Bromma. Precoated thin layer chromatography (TLC) silica gel 60 plates were obtained from BDH. All chemicals and reagents used were of analytical grade.

Synovial fluids (SF) were obtained from patients with active classical or definite rheumatoid arthritis (RA) by arthrocentesis. This material was centrifuged at 4° C. to remove cells and debris, pooled and stored in polypropylene tubes at −70° C. until required.

All purification procedures were carried at at 4° C. Pooled synovial fluid (510 ml) was dialyzed against 5 mM buffer, pH 5.0, for 24 h. The resultant precipitate was redissolved in 0.5 M acetate buffer, pH 5.00, and applied to a 200 ml column of CM Sephadex C50 which had been equilibrated with the same buffer. The column was sequentially eluted with 0.5 M acetate buffer, 5.0; 0.3 M NaCl in 0.2 M Tris-HCl, pH 8.5; and 3 M The PLA$_2$ was eluted in the latter buffer. Fractions containing PLA$_2$ activity were pooled, dialyzed against 0.05 M Tris-HCl, pH 8.5, and lyophilized. The lyophilized residue was reconstituted in 0.05 M Tris-HCl buffer, pH 8.5, continuing 2 M NaCl and chromatographed on a 1.6×68 cm Sephadex G75 column, which had been equilibrated with the same buffer. The column was eluted at 20 ml/h and fractions of 2.8 ml were collected for determination of PLA$_2$ activity and protein content. Active fractions were pooled, dialyzed against 0.05 M Tris-HCl, pH 8.5, and lyophilized. The residue was dissolved in 0.0625 M Tris-HCl, pH 9.5, containing 1% SDS and 10% glycerol, incubated for 1 h at 37° C. and applied to a 15% polyacrylamide gel. Preparative electrophoresis was carried out at 30 mA for 4 h. The gel was cut into 0.5 cm strips. The protein was crushed and eluted with 0.1 M Tris-HCl buffer, pH 7.5. Fractions containing PLA$_2$ activity were pooled and lyophilized. The steps of purification and enrichment are summarized in Table 1.

TABLE 1

| Purification step | Protein (mg) | Total activity (nmol/min) | Specific activity (nmol/min · mg protein) | Purification | Yield (%) |
|---|---|---|---|---|---|
| Synovial fluid | 21,930 | 18,717 | 0.85 | 1 | 100 |
| Dialysis | 6,528 | 13,702 | 2.09 | 2.5 | 73 |
| CM-Sephadex C-50 | 6.6 | 3,388 | 513.33 | 603.9 | 18 |
| Sephadex G-75 | 1.0 | 2,046 | 2,046.00 | 2,407.1 | 11 |
| Preparative SDS-PAGE | 0.195 | 758 | 3,887.18 | 4,573.2 | 4 |

Polyacrylamide gel electrophoresis (PAGE) in 15% polyacrylamide gels was performed in the presence of 0.1% SDS as described by Laemmli (1970) Nature 227:680681. Ovalbumin, carbonic anhydrase, trypsin inhibitor, and lactalbumin were used as molecular weight markers. The samples were incubated in 0.0625 M Tris-HCl, pH 6.8, containing 2% SDS and 10% glycerol with 5% 2-mercaptoethanol (2-ME) for 6 min at 100° C. for analytical PAGE or without 2-ME for 1 h at 37° C. for preparative SDS-PAGE, and then applied to the gel. Electrophoresis was performed for 4 h at 30 mA and the protein bands were stained with Coomassie brilliant blue or Bio-Rad silver stain. Switzer et al. (1975) Anal. Biochim. 98:231–237.

Polyacrylamide gel electrophoresis of the post G-75 fraction (1.5 mcg) in the presence of sodium dodecyl sulfate and 2-mercaptoethanol indicated the presence of two protein bands corresponding to molecular weights of 17 K and 15 K. An identical electrophoretic pattern was obtained for the same preparation of $PLA_2$, without reduction of disulfate bonds. $PLA_2$ activity was associated with both the 15K and 17K bands.

Protein determinations for all $PLA_2$ preparations described in Examples I.A. or II, except eluates from SDS-PAGE, were performed by the Bio-Rad method. Bradford (1976) Anal. Biochem. 72:248–254. The protein eluted from SDS-PAGE was assayed by the method of Lowry following trichloroacetic acid precipitation. Peterson (1977) Anal. Biochim. 83:346–356. Bovine serum albumin served as a protein standard for both methods.

B. Final purification

The material from the initial purification was loaded onto a reverse-phase C-4 HPLC column and eluted with a 15–60% acetonitrile gradient in the presence of 0.1% trifluoroacetic acid. The eluted fractions were assayed for $PLA_2$ activity (C, below), and the active fractions were pooled and lyophilized overnight in a siliconized Falcon #2059 tube. The peaks of activity, termed peaks A, B and C, were obtained routinely and were further purified separately (FIG. 2). The lyophilized peak material was resuspended in a PAGE loading buffer (2.3% SDS, 50 mM Tris, 10% glycerol), heated at 90° C. for 3 min, and loaded onto a 12.5% acrylamide minigel. Then 40,000 dpm of $^{125}I$-labeled porcine propancreatic $PLA_2$ was included within the sample as an autoradiographic marker. After electrophoresis, the gel was autoradiographed for 30 min, and the gel was cut into 1.0 mm slices, using the autoradiogram as a cutting guide. The slices were crushed and the activity was eluted in 10 mM n-ethyl-morpholino acetate, pH 7.0, for 1–2 days. Assays were performed on 1.0 μl of the eluate after 60 min incubation at 37° C., and an activity profile was obtained (FIG. 2). Peaks A, B and C all eluted from the slices corresponding to 15,000 MW, just ahead of the propancreatic marker. Active fractions were spotted and dried directly onto quaternary amine glass fiber filter paper. The filters then were washed four times in the same buffer, 5 min each, 38 and dried. Sequence analyses were performed via Edman degradation on an Applied Biosystems gas phase sequencer. The $NH_2$-terminal sequences of $sPLA_2$ type A (peak A) and $sPLA_2$ type B (peak B) are shown in FIG. 1.

C. Phospholipase $A_2$ assays

Standard assay conditions for final purification steps consisted of 50 mM Tris, pH 8.0, 150 mM NaCl 5.0 mM $CaCl_2$, 0.04% sodium deoxycholate (DOC), and 0.22 nmoles of 1-stearoyl-2-[1-$^{14}C$]Arachidonyl-L-3-phosphatidylcholine (PC, Amersham #CFA.655) as substrate, incubated at 37° C. for 30 min. The substrate was prepared by dissolving freshly desiccated PC in 2% DOC, which was then diluted to the appropriate concentration in assay buffer. The 50 μl reaction was started by the addition of prewarmed substrate and terminated by the addition of 10 μl 8 M acetic acid. Fifty microliters of the reaction mixture was spotted and dried onto Whatman thin-layer chromatography plates, and the plates were chromatographed using chloroform:methanol:acetic acid (90:10:1) as a solvent. The dried plates were exposed overnight with X-ray film, or alternatively the bands corresponding to product (arachidonate) and substrate (PC) were scraped and counted in scintillation fluid.

II. Characterization of Synovial $PLA_2$

The material prepared in Example I.A. was further characterized as described below.

A. pH Dependence and Substrate Specificity

Phospholipase activity was quantitated by the modified method [Vadas et al. (1980) Life Sci. 26:1721–1729] of Franson et al. (1978) J. Lipid Res. 19:18–23, using autoclaved *Escherichia coli*, strain $K_{12}C_{600}$, labeled with [$^{14}C$]Oleic acid, as the substrate. Assays were performed in substrate excess, using $2.8 \times 10^8$ *E. coli* per assay, corresponding to 5.6 nmol of phospholipid with a specific activity of 4,120 cpm/nmol phospholipid. The standard reaction mixture of 1.5 ml total volume contained 10 mg BSA, 7 mM $CaCl_2$, 0.1 M Tris-HCl buffer, and [$^{14}C$]Oleate-labeled *E. coil*. Reactions were allowed to proceed for 30 min at 37° C. and were terminated by filtration through a 0.45 μm Millipore filter. Enzyme activities were corrected for non-enzymatic hydrolysis. Under conditions of substrate excess, the rate of substrate hydrolysis is linear with reaction times of up to 30 min, over a fivefold range of enzymic concentration.

Determination of phospholipase activities towards the radiolabeled synthetic substrates, dipalmitoylphosphatidylcholine, and 2-linoleoyl-1-palmitoylphosphatidylethanolamine, was carried out as described by Shakir, (1981) Anal. Biochim. 114:64–70. Standard incubation mixtures contained 750 nmol of phospholipid, 2 mM $CaCl_2$, 2 mM sodium deoxycholate (DOC), 0.09% Triton X-100, and enzyme protein in 0.1 M Tris-HCl buffer in a total volume of 400 μl. Incubations were carried out at optimal pH (see below) for 1 h at 37° C. in a shaking water bath. The reaction was stopped by addition of 2.0 ml of n-heptane:isopropanol-1 N sulfuric acid (1:4:0.1, v/v/v). Released fatty acids were extracted by the method of Shakir, (1981) Anal. Biochim. 114:64–70. $PLA_2$ activity is expressed as nmol of released fatty acid per mg of protein per h.

The pH dependence of purified $PLA_2$ was determined against dipalmitoylphosphatidylcholine and 1-palmitoyl-2-linoleoylphosphatidylethanolamine over a range of pH 5–10, using the assay of Shakir, (1981) Anal. Biochim. 114:64–70. Buffers used were of constant ionic strength: 0.1 M sodium acetate-acetic acid (pH 5–6), 0.1 M Tris-HCl (pH 7–8), and 0.1 M glycine-NaOH (pH 9–10).

The pH dependence of purified $PLA_2$ was studied over the range of pH 5–10 using two synthetic phospholipid substrates, dipalmitoylphosphatidylcholine, and 2-linoleoyl-1-palmitoylphosphatidylethanolamine. Phosphatidylethanolamine was hydrolyzed over a wide range of pH (6–10), with optimal PLA$_2$ activity evident at pH 7.5–8.0. Maximal PLA$_2$ activity for phosphatidylcholine was seen at pH 7.0 with an abrupt decrease in activity at pH 8–10.

The specific activities of PLA$_2$ were comparable for all three phospholipids tested. Membrane phospholipids of *E. coli* were hydrolyzed most actively, while phosphatidylethanolamine and phosphatidylcholine were hydrolyzed at rates of 41 and 27% respectively of that of *E. coli* phospholipid. Since detergents (especially the non-ionic Triton X-100) act as an inert matrix solubilizing the phospholipids in similar structures, the observed activities of phosphatidylethanolamine and phosphatidylcholine are directly comparable. Roberts et al. (1978) J. Biol. Chem. 53:1252–1257.

TABLE II

| Phospholipid substrate | Activity (nmol/μ protein · h) |
| --- | --- |
| *E. coli* phospholipid | 122.5 |
| Dipalmitoylphosphatidylcholine | 33.5 |
| 1-Palmitoyl-2-linoleoyl-phosphatidylethanolamine | 49.9 |

*E. coli* membrane phospholipid composition: 48.6% phosphatidylethanolamine, 25.0% phosphatidylglycerol, and 11.1% cardiolipin. Vadas & Pruzanski, (1984) Adv. Inflam. Res. 7:51–59.

B. Determination of Positional Specificity

The positional specificity of the purified enzyme was determined using 1-palmitoyl-2-[1-$^{14}$C]palmitoylphosphatidylcholine as substrate. The assay system contained 750 nmol of radioactive phosphatidylcholine dispersed in 0.1 M Tris-HCl buffer, pH 7.5, containing 2 mM CaCl$_2$, 2 mM DOC, 0.09% Triton X-100, and 100 μl of enzyme preparation in a total volume of 400 μl. The reaction was carried out at 37° C. for 3.5 h and was termination by the addition of 8 ml of chloroform-methanol (2:1, v/v). Lipids were extracted by the method of Folch et al., (1957) J. Biol. Chem. 6:497–509, and separated by TLC in chloroform-methanol-acetic acid-water (65 :25 :8 :4, v/v/v/v). The lipid spots were visualized by exposure to iodine vapor. After sublimination of the iodine, spots corresponding to authentic PC, lyso PC and free fatty acid standards were scraped into scintillation vials containing 10 ml of scintillation fluid and measured for radioactivity in a liquid scintillation spectrometer (Beckman LS7500). 1-acyl-2-[1-$^{14}$C]palmitoylphosphatidylcholine was incubated with venom PLA$_2$, crude synovial fluid or purified synovial fluid PLA$_2$ and the reactions products were analyzed by thin-layer chromatography.

Greater than 93% of the total substrate was hydrolyzed by PLA$_2$ from Crotalus adamanteus venom. Of the total products formed, 97.2% of the radioactivity was associated with free fatty acid, while only 2.8% of radioactive product comigrated with lysolecithin, consistent with preferential cleavage of the fatty acid esterified in the sn-2 position. Similarly, both crude synovial fluid and the purified preparation of PLA hydrolyzed radiolabeled substrate preferentially at the sn-2 position, yielding greater than 95% $^{14}$C-fatty acid and less than 5% 2-[$^{14}$C]palmitoylphosphatidylcholine.

In order to rule out the combined activities of a PLA$_1$ and lysophospholipase, crude synovial fluid and purified synovial fluid phospholipase were incubated as above with I-[1-$^{14}$C]palmitoylphosphatidylcholine. Thinlayer chromatographic analysis of the products revealed that 99% of the radioactive label remained associated with the lysophospholipid substrate, and only 0.05% of the radioactivity was associated with free fatty acid, indicating the virtual absence of detectable lysophospholipase activity. These data are consistent with an absolute 2-acyl specificity for synovial fluid phospholipase.

C. Effect of SDS on PLA$_2$ activity

The effect of SDS on the rate of hydrolysis of phosphatidylcholine by highly purified PLA$_2$ was studied using Shakir's method, supra. SDS inhibited PLA$_2$ activity on a concentration-dependent manner. Inhibition of PLA$_2$ was 94 and 7% of initial enzyme activity at SDS concentrations of 1 mg/ml and 0.1 mg/ml, respectively. In evaluating the utility of preparative SDS-PAGE, recovery of enzyme from the slab gel was consistently between 95–100% of the total enzyme applied to the gel. However, subsequent lyophilization of highly purified PLA$_2$ resulted in significant losses of activity (approx. 64% loss).

D. Immunoreactivity of PLA$_2$

Synovial fluid PLA$_2$ was tested for immunoreactivity against rabbit anti-human pancreatic PLA$_2$ by radioimmunoassay. Sternby et al. (1984) Biochim. Biophys. Acta 789:164–169. Ten specimens of unfractionated rheumatoid synovial fluid with PLA$_2$ activity (using *E. coli* phospholipid substrate) ranging from 8.7 to 31.0 nmol/ml.min were tested. In all cases, there was no substantial cross-reactivity with antihuman pancreatic PLA$_2$ nor did PLA$_2$ quantitation by enzyme assay and RIA correlate (r=0.134). Similarly, the antibody failed to recognize the purified (ex-Sephadex G75) fraction (Table III). The correlation of RIA and enzyme assay for porcine pancreatic PLA$_2$ added to synovial fluid was significant.

TABLE III

| | PLA$_2$ | |
| --- | --- | --- |
| Sample | Enzyme activity (nmol/ml · min) | RIA (μg/l) |
| Synovial fluid | | |
| 1 | 8.67 | <0.8 |
| 2 | 30.55 | 0.8 |
| 3 | 23.00 | 0.8 |
| 4 | 18.23 | 0.8 |
| 5 | 11.62 | <0.8 |
| 6 | 16.37 | 0.9 |
| 7 | 16.67 | 4.3 |
| 8 | 18.08 | 2.1 |
| 9 | 30.73 | 2.0 |
| 10 | 31.02 | 2.3 |
| Synovial fluid plus | | |
| 0 μg pancreatic PLA$_2$ | 38.48 | <0.8 |
| 1 μg pancreatic PLA$_2$ | 119.93 | 13.0 |
| 15 μg pancreatic PLA$_2$ | 881.98 | 51.0 |
| 30 μg pancreatic PLA$_2$ | 1,422.72 | 64.0 |
| Synovial fluid PLA$_2$ ex-Sephadex G-75 | 81.82 | <0.8 |

III. Cloning of Synovial PLA$_2$ Sequences

A. Genomic Cloning

Two 50-mer codon-preference oligos were designed from the RASF peak A sequence, minimizing ambiguity by (a) centering the oligos upon codon groups with minimal ambiguity and (b) allowing for G:T binding.

The oligos, shown in FIG. 3, were synthesized on an Applied Biosystems oligonucleotide synthesizer.

The oligos were labeled with γ-$^{32}$P-ATP and polynucleotide kinase, and then used as a hybridization probe for the EMBL3-human leukocyte genomic library obtained from Clonetech Inc. (Mountain View, CA). Then 10$^6$ total plaques were placed on twenty 150 mm agar plates containing L-broth, using bacterial strain NM538. The plaques were lifted onto nitrocellulose filters, denatured, baked 2 hours at 80° C. in a vacuum oven, and prehybridized 2 hours in prehybridization solution (5X Denhardt's, 20% formamide, 6X SSC, 50 mM NaPO$_4$, 100 μg/ml sheared salmon sperm DNA) at 37° C. Hybridization was overnight at 37° C. in prehybridization solution plus 10% dextran sulfate and 2×10$^6$ cpm of labeled probe. The filters were washed twice at 25° C. in 1X 0.16 M NaCl, 0.016 M sodium citrate (SSC), 0.1% sodium docecyl sulfate (SDS), and then once in the same solution at 50° C. for 1 hour and then exposed to autoradiographic film overnight at −70° C. Later, the same filters were rewashed at 55° C. and reexposed.

Two classes of signals were seen, 7 of which hybridized to both probes, and 4 of which hybridized to probe 2779 only. All 11 signals were plaque-purified through three rounds of purification. When phage DNA was prepared from the clones and analyzed by agarose gel separation of restriction enzyme digests, the number of distinct clones was reduced to 2, henceforth represented by clones 6 and 10. Oligo 2779 hybridized strongly when washed at 55° C. to clone 6 and 10; oligo 2780 hybridized weakly to clone 6 under these same conditions.

DNA from the two unique clones was digested with endonucleases HaeIII, RsaI, and AluI. The completed digest was extracted with phenol/chloroform and precipitated with ethanol. The dried pellets were resuspended in 10 mM Tris, pH 8.0, 1 mM EDTA, and 1.0 μl aliquots were ligated to bacteriophage M13mp8, which had been previously digested with SmaI. The transformed E. coli strain JM101 cells were plated onto 150 mm L-agar plates and incubated overnight at 37° C. The resulting M13 recombinant plaques were lifted and the filters hybridized as described above. Plaques coinciding with hybridization signals were picked and used to produce single-stranded M13 DNA templates. Sequencing of the clones was done using the dideoxy/enzymatic method, and the resulting sequences were aligned and analyzed on a VACS 8500 computer (Digital Corp.) using the Intelligenetics programs Seq and Gel (Intellicorp Inc., Mountain View, CA). The resulting clone sequences for exons of the two unique phospholipase clones 6 and 10 are shown in FIG. 4. They are contained within a 404 bp AluI fragment (clone 6) and an approximately 460 bp AluI fragment (clone 10). Clones 6 and 10 have been renamed λSPLA2-6 and λSPLA2-10, respectively.

The sPLA$_2$ coding sequence in λsPLA2-6 was originally believed to be exon 2 of the human type A gene type A. The cDNA sequence identified in III.B, below, was used to identify the remaining exons in the genomic clones. It was found that an unexpected intron existed in the 5′-noncoding region of the gene. Thus, what was originally believed to be exon 2 is actually exon 3. The sequence encoding exon 1 is shown in FIG. 7. Bases 1016 through 1038 match bases 8 to 27 of the cDNA clone exactly. Although the precise start of transcription has not been determined, its most likely location is at or shortly upstream of base 1012. A potential "TATA" sequence can be seen at nucleotides 968 through 974, and a putative "CAAT" sequence lies at nucleotides 904 through 909.

B. cDNA Cloning

A 60-mer oligonucleotide probe was synthesized to match the nucleotide sequence for λsPLA2-6 shown in FIG. 4 and corresponding to the codons for amino acid residues 5-24 shown in FIG. 1. This oligonucleotide probe was used to screen RNA blots from various sources, including cell lines HL60 and U937, human synovial cells, human peritoneal inflammatory exudate cells, human pus cells, porcine jejunum tissue, porcine pancreatic tissue, rat spleen tissue, and rat liver tissue. Significant levels of RNA was detected by hybridization in human peritoneal cells and, to a lesser extent, human synovial cells.

A cDNA library was constructed from polyA+ message from a peritoneal cell RNA prep according to the method of Gubler & Hoffman (1983) Gene 25:263-269. The library was screened with the 60-mer probe, and 17 discrete duplicating signals were obtained after washing the filters in 1X SSC, 0.1% SDS at 60° C. DNA from ten of the clones was subjected to analysis by PAGE. All of the clones contained inserts of 800 to 1,000 bp. Four of the clones, designated 1, 4, 11 and 14, were selected for subcloning into bacteriophage M13 and subsequent DNA sequence analysis by standard techniques. One of these clones, designated λsPLA$_2$cDNA-4 was determined to encode the entire sPLA$_2$ type A sequence. See FIG. 6. The other clones contained the same sequence or varied slightly in length at the 5′ end and had different length polyA tails. Otherwise, the clones were identical except for a C to T change at position 277, a silent mutation with respect to the amino acid specified by the codon. A typical translation termination sequence, AATAAA, can be seen beginning at base 116. The mature peptide sequence encoded by λPLA2cDNA-4 contains 124 amino acids, and has a calculated molecular weight and pI of 13,919 and 6.46, respectively.

IV. Recombinant Synovial PLA$_2$

A. Bacterial Hosts

Active recombinant sPLA$_2$ was produced in bacteria, such as E. coli, as a β-galactosidase fusion protein employing a procedure adapted from de Geus et al. (1987) Nucleic Acids Res. 15:3743-3759. This methodology was adapted to sPLA$_2$ as follows. First, a single base change from C to G introduced at the C-terminus in nucleotide 588 created a HindIII site 17 bases downstream from the TGA stop codon. This change was made via oligonucleotide-directed mutagenesis of single-stranded M13 DNA, using standard molecular biology methodology. Digestion of this mutagenized clone DNA with BclI and HindIII yielded a 370 bp fragment containing the entire sPLA$_2$ coding region with the exception of the first nine amino acid residues of the mature protein. These nine residues, along with a cleavable fusion site (Trp) and an EcoRI site were replaced with the two oligonucleotide linkers shown in FIG. 8. The expression construct p86-1A was obtained by ligating the 370 bp BclI-HindIII fragment along with the two oligonucleotides into expression vector pHNF86 which had been previously cut with EcoRI and HindIII. The pHNF86 vector consists of a pBR322 backbone, the *E. coli* tryptophan promoter, a ribosomal binding site, sequences encoding a portion of the amino terminal portion of the *E. coli* β-galactosidase gene followed by six Thr residues, an EcoRI and HindIII site, and two strong *E. coli* transcription termination signals. See, e.g., Sung et al (1986) *Proc. Natl. Acad. Sci. USA* 83:561–565.

The resulting expression vector containing the $PLA_2$ construct was then used to transform *E. coli* strain W3110 (ATCC accession no. 27325) for expression. After inoculation of a culture of transformed cells of a suitable population density, expression was induced by the addition of 3-B-indoleacrylic acid into the media. After 9 hours of growth in induction media, inclusion bodies were observed in about 90% of the cells. After cell disruption, the inclusion bodies were then pelleted and boiled 5 min in gel loading buffer containing 50 mM β-mercaptoethanol. By comparison with gels of similar extracts from uninduced and control cultures, a prominent 15 kD band was observed in the induced cultures transformed with the expression construct. This band was highly enriched in gels from extracts of purified inclusion bodies, allowing large-scale isolation of this fusion protein from preparative SDS-polyacrylamide gels. Fusion protein prepared in this manner was injected into rabbits, rats and mice for the production of antibodies.

Purified fusion protein fractions may be activated by the S-sulfonation procedure as described by DeHaas et al. (1987), supra. After activation, the fusion protein can be cleaved at the Trp residue to release the mature human $PLA_2$. Alternatively, the two steps in reverse order may give greater yields of active protein See, e.g., Lishchwe & Ochs (1982) Anal. Biochem 127:453–457 A further conventional purification step can then be used to separate the $sPLA_2$ from the β-gal leader.

B. Vaccinia Virus

Recombinant $sPLA_2$ polypeptides can also be provided in mammalian cells using a vaccinia virus expression vector. Such expression vectors are well known in the art. See, e.g., PCT Pub. No. WO 86/07593 (CBI:PB8).

For example, the vaccinia expression vector pSC-11, described in Chakrabarti (1985) *Mol. Cell. Biol.* 5:3403, was employed according to the following protocol. An $sPLA_2$ coding fragment was prepared as described above, except that base 127 was changed from A to G via oligonucleotide-directed mutagenesis to produce a SacI site 5 bp upstream from the initiation ATG codon. The coding region is thus contained on a 469 bp SacI-HindIII fragment. This fragment was then blunt-end ligated into vaccinia vector pSC-11, previously cut with SmaI. The resulting DNA was recovered and used to transfect vaccinia-infected monolayers of cultured mammalian CV-1 cells using standard procedures. The resulting plaques were purified through several rounds of infection.

Figure 9:
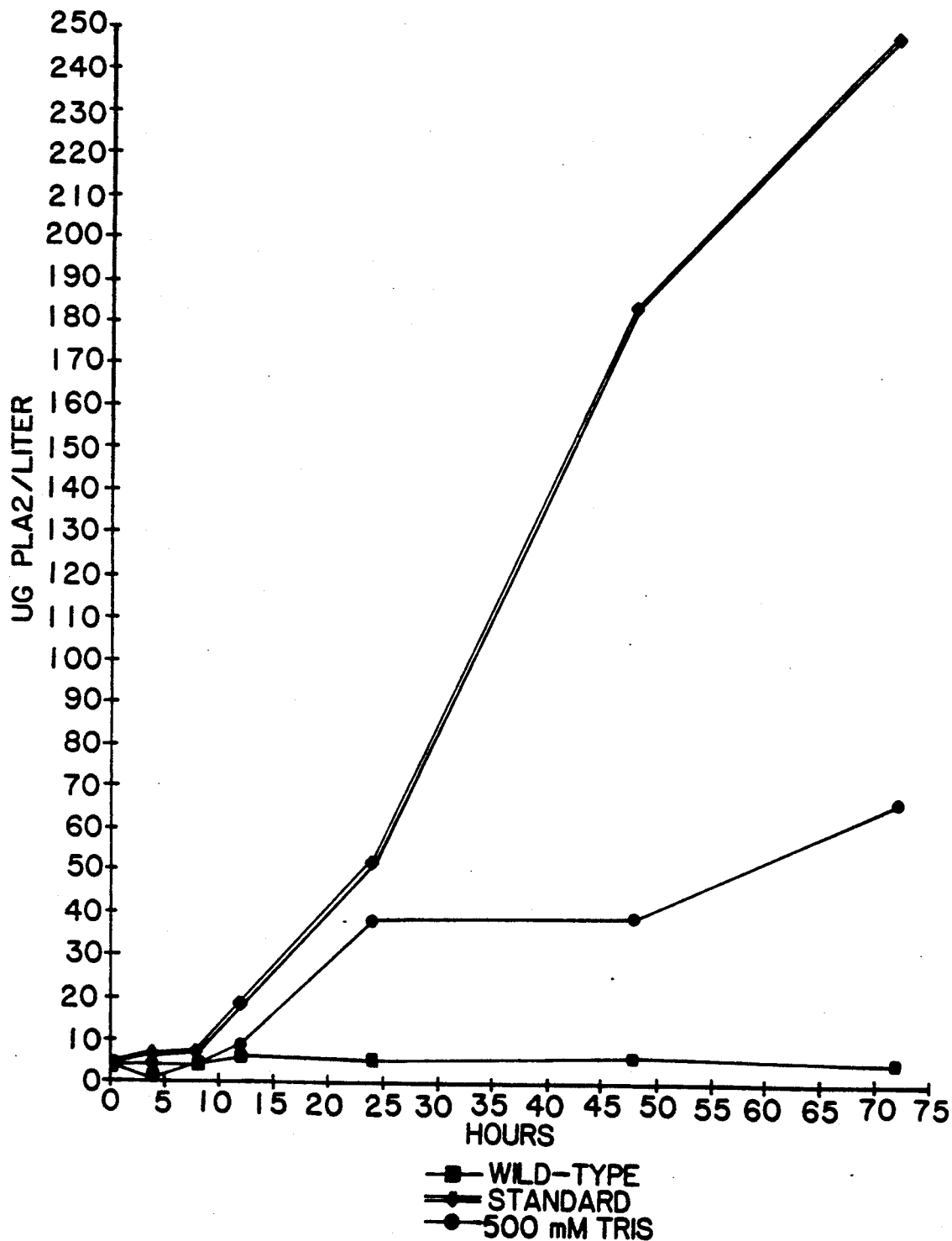
FIG. 9 graphically depicts the accumulation of PLA$_2$ enzyme activity in serum-free medium during infection of CV-1 cells by recombinant vaccinia virus containing the human sPLA$_2$ type A gene.

As shown in FIG. 9, assays of $PLA_2$ activity present in both cells and media showed significant accumulation of $PLA_2$ in the media with time. Large quantities of media prepared in a similar manner can be obtained, and the active recombinant $PLA_2$ enzyme expressed by these cells can thus be obtained by standard purification procedures. In addition, the infectious virus purified from these cells was used to vaccinate rabbits and mice for the production of antibodies recognizing the active enzyme. When a significant titer is achieved in mice, monoclonal antibodies blocking the enzyme activity can be identified by screening hybridoma clones for the ability to block activity in the $PLA_2$ assays described above.

While the present invention has been illustrated above by certain specific embodiments, it is not intended that these specific examples should limit the scope of the invention as described in the appended claims.

We claim:

1. A composition consisting essentially of a double-stranded DNA construct containing a heterologous region comprising a coding sequence for a mammalian synovial phospholipase $A_2$.

2. The composition of claim 1 wherein said coding sequence encodes the amino acid sequence of mature mammalian synovial phospholipase $A_2$.

3. The composition of claim 1 wherein said coding sequence encodes the amino acid sequence of the preenzyme.

4. The composition of claim 1 wherein said mammalian synovial phospholipase $A_2$ is human synovial phospholipas $A_2$.

5. The composition of claim 1, wherein said mammalian synovial phospholipase $A_2$ is a mutein wherein the amino acid residue corresponding to $His_{48}$ in the native mammalian synovial phospholipase $A_2$ is replaced with an amino acid residue other than His.

6. The composition of claim 5 wherein said amino acid corresponding to His $_{48}$ is Glu or Asp.

7. The composition of claim 1 wherein said DNA construct further comprises a replicon.

8. The composition of claim 7 wherein said replicon is a bacterial plasmid.

9. The composition of claim 7 wherein said replicon is a yeast plasmid.

10. The composition of claim 7 wherein said replicon is a bacteriophage.

11. The composition of claim 7 wherein said replicon is a chromosome.

12. A method of producing a recombinant mammalian synovial phospholipase $A_2$ comprising:

providing a population of transformed cells containing a replicon functional in said cells, said replicon comprising a coding sequence under the control of a promoter functional in said cells, said coding sequence encoding a mammalian synovial phospholipase $A_2$, said population being substantially free of other cells;

growing said population under conditions whereby said mammalian synovial phospholipase $A_2$ is expressed; and recovering said mammalian synovial phospholipase $A_2$.

13. The method of claim 12 wherein said cells are bacterial cells.

14. The method of claim 12 wherein said cells are yeast cells.

15. The method of claim 12 wherein said cells are mammalian cells.

16. The method of claim 13 wherein said replicon is a plasmid.

17. The method of claim 14 wherein said replicon is a plasmid.

18. The method of claim 15 wherein said replicon is a chromosome.

19. The method of claim 12 wherein said mammalian synovial phospholipase $A_2$ is human synovial phospholipase $A_2$.

20. A composition comprising isolated mammalian phospholipase $A_2$.

21. A composition according to claim 20 wherein said mammalian synovial phospholipase $A_2$ is mammalian synovial phospholipase $A_2$ type A.

22. A composition according to claim 20 wherein said mammalian synovial phospholipase $A_2$ is mammalian synovial phospholipase $A_2$ type B.

23. A composition according to claim 20 wherein said mammalian synovial phospholipase $A_2$ is mammalian synovial phospholipase $A_2$ type C.

24. A composition according to claim 20, wherein said mammalian synovial phospholipase $A_2$ is a mutein and further wherein the amino acid residue corresponding to $His_{48}$ in the native mammalian synovial phospholipase $A_2$ is replaced with an amino acid residue other than His.

25. A composition according to claim 24 wherein said amino acid corresponding to $His_{48}$ is Glu or Asp.

* * * * *